US012383401B2

(12) United States Patent
Watson et al.

(10) Patent No.: US 12,383,401 B2
(45) Date of Patent: Aug. 12, 2025

(54) VALVE IMPLANT, DELIVERY SYSTEM AND METHOD

(71) Applicants: APPARENT LLC, Santa Rosa, CA (US); SINGAPORE HEALTH SERVICES PTE LTD, Singapore (SG)

(72) Inventors: James R. Watson, Santa Rosa, CA (US); Khung Keong Yeo, Singapore (SG)

(73) Assignees: APPARENT LLC; SINGAPORE HEALTH SERVICES PTE LTD, Singapore (SG)

( * ) Notice: Subject to any disclaimer, the term of this patent is extended or adjusted under 35 U.S.C. 154(b) by 987 days.

(21) Appl. No.: 17/270,087

(22) PCT Filed: Aug. 22, 2019

(86) PCT No.: PCT/SG2019/050415
§ 371 (c)(1),
(2) Date: Feb. 22, 2021

(87) PCT Pub. No.: WO2020/040699
PCT Pub. Date: Feb. 27, 2020

(65) Prior Publication Data
US 2021/0322168 A1    Oct. 21, 2021

Related U.S. Application Data

(60) Provisional application No. 62/721,428, filed on Aug. 22, 2018.

(51) Int. Cl.
*A61F 2/24* (2006.01)
*A61F 2/95* (2013.01)

(52) U.S. Cl.
CPC .......... *A61F 2/2439* (2013.01); *A61F 2/2418* (2013.01); *A61F 2/2436* (2013.01);
(Continued)

(58) Field of Classification Search
CPC .... A61F 2/2439; A61F 2/2418; A61F 2/2436; A61F 2002/9511; A61F 2230/0006; A61F 2230/0008
See application file for complete search history.

(56) References Cited

U.S. PATENT DOCUMENTS 4,994,077 A * 2/1991 Dobben ................ A61F 2/2406
623/2.38
6,299,637 B1 * 10/2001 Shaolian ............... A61F 2/2475
623/1.24
(Continued)

FOREIGN PATENT DOCUMENTS

DE    102013017750 A1    4/2015
EP        2633821 A2    9/2013
WO     2017217932 A1    12/2017

OTHER PUBLICATIONS

Extended European Search Report dated Apr. 28, 2022 for European Application No. 19852510.7.
(Continued)

*Primary Examiner* — Elizabeth Houston
*Assistant Examiner* — Jonathan A Hollm
(74) *Attorney, Agent, or Firm* — JCIP; Joseph G. Chu

(57) ABSTRACT

A valve implant includes a valve leaflet prosthesis having a wire frame, a leaflet blade panel attached to the wire frame, and one or more tether struts extending from the wire frame, and a stent having a first end portion and a second end portion along a longitudinal stent axis, and a flexible extended stent strut extending longitudinally from the first end portion, wherein the one or more tether struts of the valve leaflet prosthesis is rotatably coupled to the flexible extended stent strut in a manner such that the one or more tether struts are rotatable about a rotational axis which is parallel to the one or more tether struts and which extends transverse to the longitudinal stent axis. A delivery system (Continued)

for the valve implant and a method of preparing the delivery system are also disclosed.

15 Claims, 19 Drawing Sheets

(52) U.S. Cl.
CPC .............. *A61F 2002/9511* (2013.01); *A61F 2230/0006* (2013.01); *A61F 2230/0008* (2013.01)

(56) References Cited

U.S. PATENT DOCUMENTS

| 2005/0177228 | A1* | 8/2005 | Solem | A61F 2/2451 |
| | | | | 623/2.36 |
| 2006/0241745 | A1* | 10/2006 | Solem | A61F 2/2442 |
| | | | | 623/2.18 |
| 2013/0261737 | A1* | 10/2013 | Costello | A61F 2/2418 |
| | | | | 623/2.11 |
| 2013/0325110 | A1* | 12/2013 | Khalil | A61F 2/2466 |
| | | | | 623/2.11 |
| 2017/0056174 | A1 | 3/2017 | Tobis et al. | |

OTHER PUBLICATIONS

International Search Report and Written Opinion of International Searching Authority for International Application No. PCT/SG2019/050415.

* cited by examiner

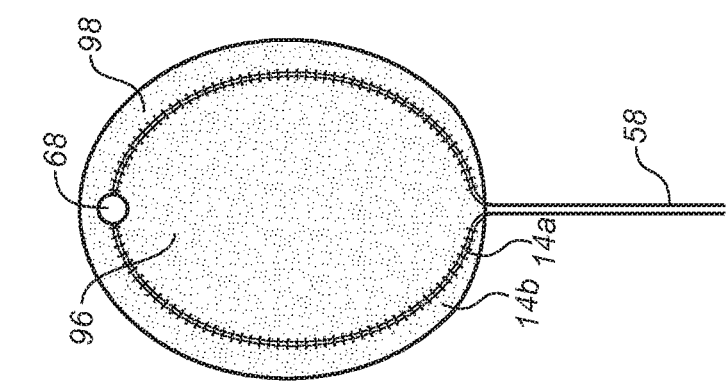
FIG. 8A    FIG. 8B
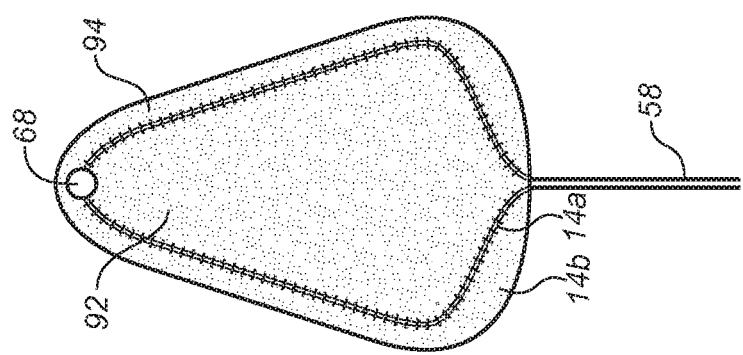
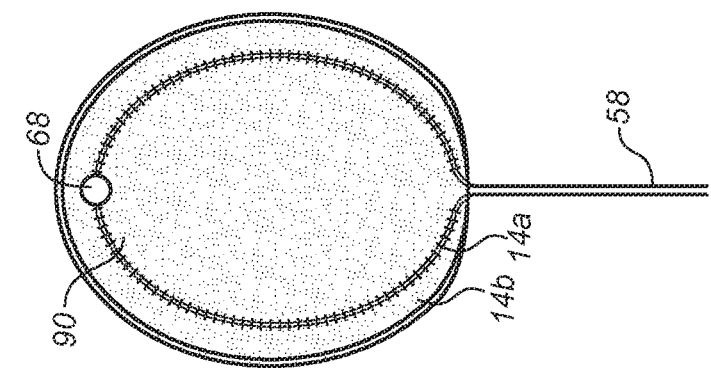
FIG. 7B
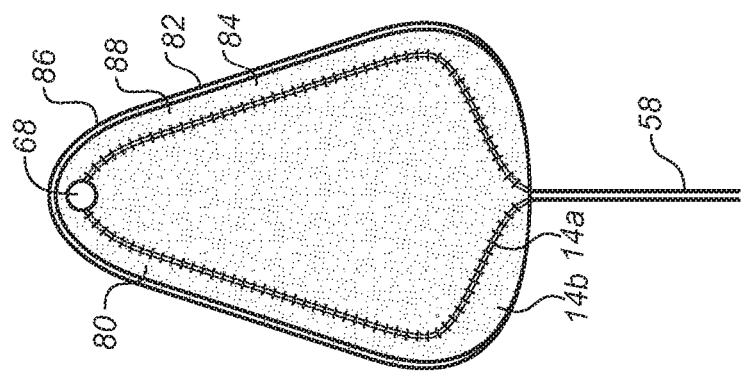
FIG. 7A

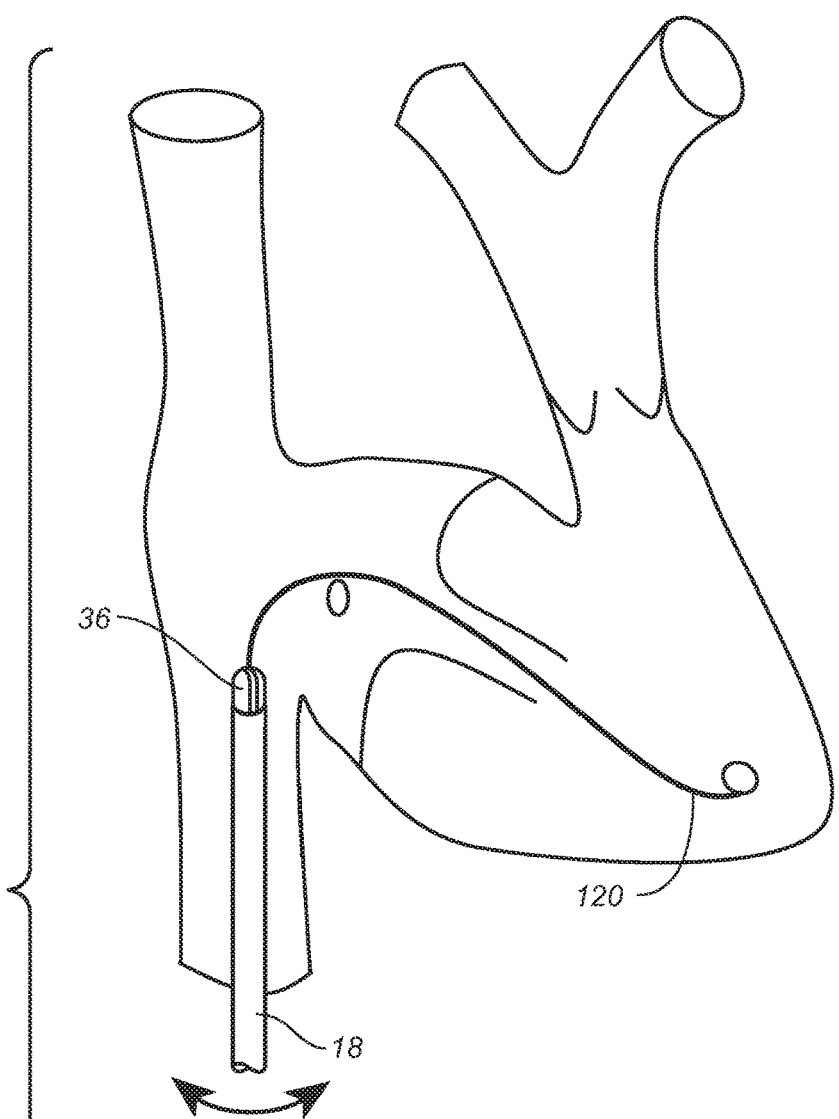
FIG. 13A
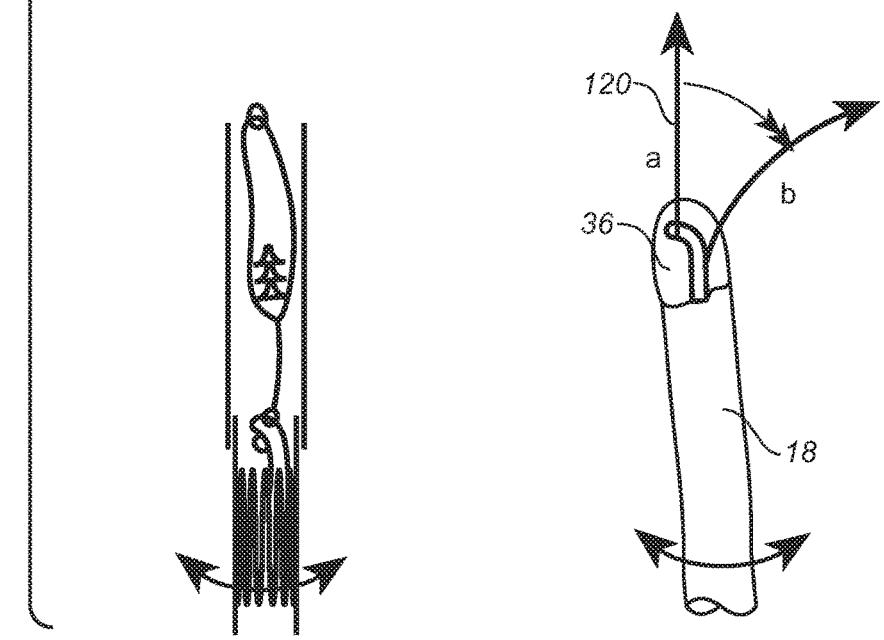

VALVE IMPLANT, DELIVERY SYSTEM AND METHOD

CROSS-REFERENCE TO RELATED APPLICATIONS

The present application claims the benefit of the U.S. provisional patent application No. 62/721,428 filed on 22 Aug. 2018, the entire contents of which are incorporated herein by reference for all purposes.

TECHNICAL FIELD

Various embodiments generally relate to a valve implant, a delivery system for the valve implant, a method of preparing the delivery system, and a method of implanting the valve implant.

BACKGROUND

Historically, valvular insufficiency, such as tricuspid regurgitation (TR), was repaired using open-heart procedures. These high risk procedures, performed under general anesthesia, typically involve providing circulatory support by a heart-lung bypass machine, as the patient's heart is stopped during surgery. Risks are significant and recovery is painful and difficult.

Accordingly, the preferred valve repair procedure for TR is increasingly performed using significantly less invasive percutaneous transluminal valve replacement procedures, as these procedures dramatically reduce the risks of open-heart surgery. In principle, replacement valves are configured to function much as the diseased valve being replaced, including valve leaflets. Thus, when using mechanical replacement valves, the procedure involves sizing the replacement valve for a patient-specific fit.

Delivery of mechanical replacement valves, such as tricuspid valves, entails loading the valve onto a delivery device, such as an on-the-wire or over-the-wire catheter in a compressed configuration, passing it percutaneously to the affected area, positioning and securing it, and then removing the delivery device to complete the deployment. The replacement valve is then sewed to secure it in place.

Accordingly, there is a need for a simpler and easier solution for heart valve replacement.

SUMMARY

According to various embodiments, there is provided a valve implant. The valve implant may include a valve leaflet prosthesis having a wire frame, a leaflet blade panel attached to the wire frame, and one or more tether struts extending from the wire frame. The valve implant may include a stent having a first end portion and a second end portion along a longitudinal stent axis, and a flexible extended stent strut extending longitudinally from the first end portion. The one or more tether struts of the valve leaflet prosthesis may be rotatably coupled to the flexible extended stent strut in a manner such that the one or more tether struts are rotatable about a rotational axis which is parallel to the one or more tether struts and which extends transverse to the longitudinal stent axis.

According to various embodiments there is provided a delivery system for the valve leaflet implant as described herein. The delivery system may include a delivery device. The delivery device may include an outer sheath. The delivery device may further include an inner catheter inserted into the outer sheath in a manner so as to be slidable relative to the outer sheath, wherein the inner catheter has a guidewire lumen extending throughout an entire length of the inner catheter and includes a stent carrier arrangement at an end portion of the inner catheter. The delivery device may further include a nosecone assembly having a nosecone-rod extending longitudinally from an end of the inner catheter and a nosecone disposed at an end of the nosecone-rod, wherein the nosecone includes a leaflet-prosthesis-alignment-element. The delivery device may include a guidewire insertion tool extending longitudinally and coaxially from an end of the guidewire lumen of the inner catheter so as to serve as a continuation of the guidewire lumen. According to various embodiments, the delivery system may include the valve implant as described herein. For example, the valve implant may include a valve leaflet prosthesis having a wire frame, a leaflet blade panel attached to the wire frame, and one or more tether struts extending from the wire frame. The valve implant may include a stent having a first end portion and a second end portion along a longitudinal stent axis, and a flexible extended stent strut extending longitudinally from the first end portion. The one or more tether struts of the valve leaflet prosthesis may be rotatably coupled to the flexible extended stent strut in a manner such that the one or more tether struts are rotatable about a rotational axis which is parallel to the one or more tether struts and which extends transverse to the longitudinal stent axis. According to various embodiments, in the delivery system, the stent of the valve implant may be compressed to wrap around the stent carrier arrangement, the flexible extended stent strut may be bent so as to align the one or more tether struts of the valve leaflet prosthesis longitudinally with respect to the stent, and the valve leaflet prosthesis of the valve implant may be compressed into an elongate shape and placed in engagement with the leaflet-prosthesis-alignment-element of the nosecone.

According to various embodiments, there is provided a method of preparing the delivery system as described herein for delivering the valve implant as described herein. The method may include inserting a guidewire, in a front loading manner, through the guidewire insertion tool and through the guidewire lumen of the inner catheter. The method may include removing the guidewire insertion tool from the delivery system such that the guidewire remains inserted through the guidewire lumen of the inner catheter.

According to various embodiments, there is provided a method of implanting the valve implant as described herein in valve repair procedure for tricuspid regurgitation using the delivery system as described herein. The method may include directing a first end of a guidewire via inferior vena cava access through a right atrium of the heart and into a right ventricle of the heart such that a final segment of the guidewire curves from the inferior vena cava, through the right atrium and into the right ventricle. The method may include inserting a second end of the guidewire in to the delivery system, in a front loading manner, through the guidewire insertion tool and through the guidewire lumen of the inner catheter. The method may include removing the guidewire insertion tool from the delivery system such that the guidewire remains inserted through the guide hole arrangement of the leaflet structure and through the guidewire lumen of the inner catheter. The method may include advancing the delivery system along the guidewire until the nosecone is at a transition region between the inferior vena cava and the right atrium. The method may include advancing the inner catheter relative to the outer sheath in a manner such that, as the nosecone advance away from a corresponding end of the outer sheath in a straight path, the valve leaflet prosthesis dislodges from the leaflet-prosthesis-alignment-element of the nosecone, expands into an original shape and continue to advance along the final segment of the guidewire curving into the right ventricle in a manner so as to be positioned alongside native tricuspid leaflets of the heart. The method may include retracting the outer sheath relative to the inner catheter in a manner such that, as the outer sheath retreats to expose the stent, the stent expands and dislodges from the stent carrier arrangement in a manner so as to be anchored to the inferior vena cava. The method may include withdrawing the guidewire and the delivery system.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIGS. 7A-7B are plan views showing possible two ply valve leaflet prosthesis with differentially sized edges according to various embodiments;

FIGS. 8A-8B show two ply valve leaflet prostheses with approximated edges according to various embodiments;

FIG. 13A is a schematic view showing advancement of the delivery system to the RV over a guidewire according to various embodiments;

DETAILED DESCRIPTION

Figure 1:
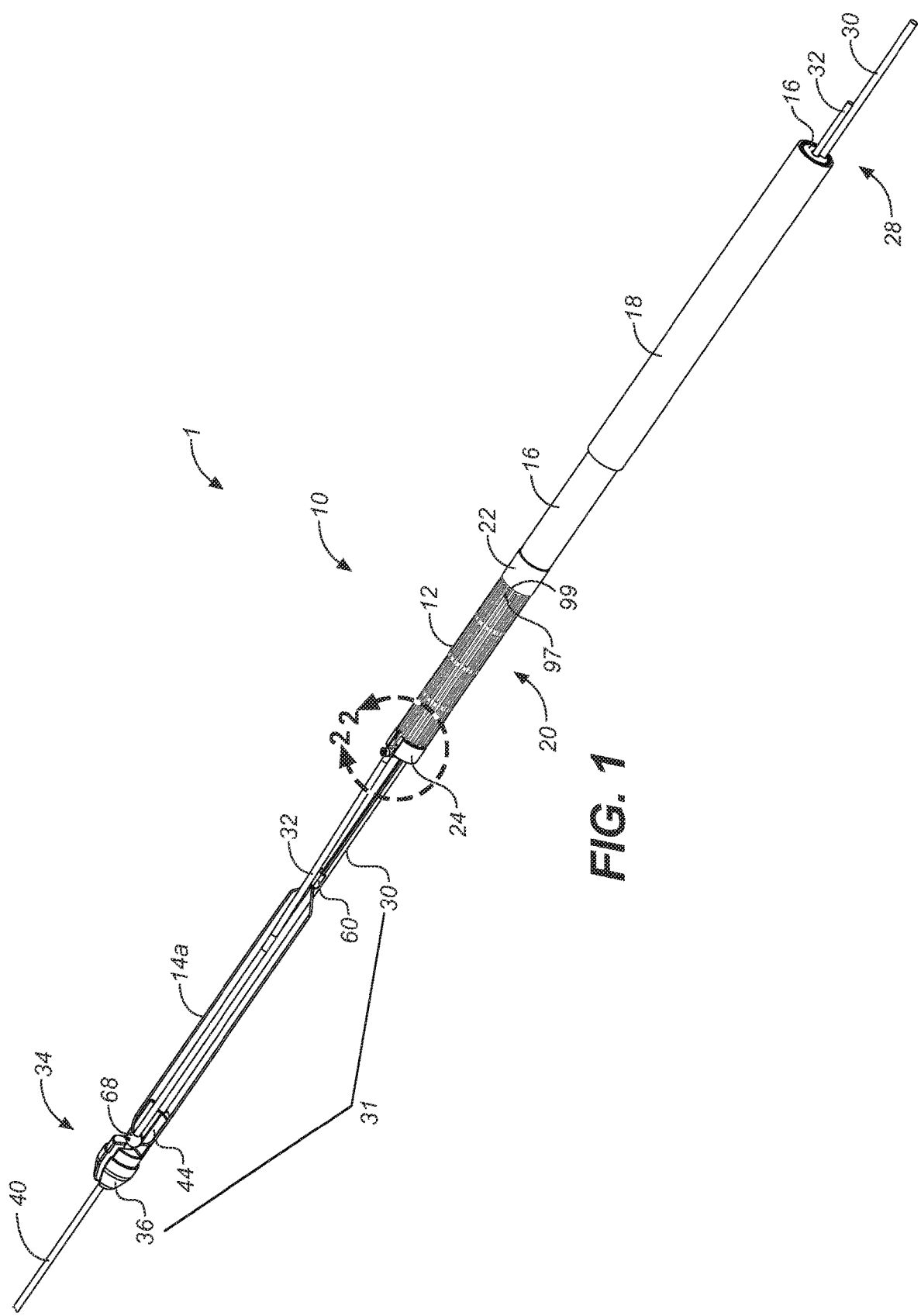
FIG. 1 is an upper perspective view of a delivery system with a prosthesis frame (or a wire frame of a valve leaflet prosthesis) and a stent loaded for delivery according to various embodiments.

Embodiments described below in the context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure. In addition, the singular terms "a", "an", and "the" include plural references unless context clearly indicates otherwise. Similarly, the word "or" is intended to include "and" unless the context clearly indicates otherwise.

Various embodiments generally relate to a valve implant (or a valve replacement assembly or a replacement valve). According to various embodiments, the valve implant (or the valve replacement assembly or the replacement valve) may be used to replace a diseased valve within a heart. According to various embodiments, the valve implant (or the valve replacement assembly or the replacement valve) may be used for valve replace procedure for tricuspid regurgitation (TR). Various embodiments generally also relate to a delivery system for the valve implant (or the valve replacement assembly or the replacement valve). According to various embodiments, the delivery system may be configured to percutaneously deliver the valve implant (or the valve replacement assembly or the replacement valve) into the heart for replacing the diseased valve. Various embodiments further relates to a method of preparing the delivery system, and a method of implanting the valve implant (or the valve replacement assembly or the replacement valve). Various embodiments relates most generally to method and devices in interventional cardiology, and more particularly to valve leaflet prostheses and stents to address aortic valve regurgitation, and still more particularly to a tricuspid valve leaflet prosthesis movably coupled to a stent.

To eliminate the need for sewing the replacement valve (or the valve implant or the valve replacement assembly) to secure it in place, various embodiments include tethering a replacement valve leaflet prosthesis to an expandable anchoring stent placed upstream of the valve leaflet prosthesis in native circulatory tissue. According to various embodiments, the valve implant (or a valve replacement assembly or a replacement valve) may have an optimal operational movement (opening and closing) under the flow conditions in every cardiac cycle roughly 40 million times per year, i.e., movement that closely replicates native valve leaflet movement to maintain unidirectional blood flow through the valve.

According to various embodiments, there is provided a valve implant (or a valve replacement assembly or a replacement valve), deployed in a percutaneous transluminal procedure, in which a replacement valve leaflet prosthesis is tethered to an anchoring stent without having its functional movements adversely affected by the stent tether. According to various embodiments, there is further provided a delivery system adapted to deploying such an implant or assembly.

Accordingly, various embodiments are described herein that relate to devices and methods for operatively tethering a prosthetic heart valve leaflet to an expandable anchoring stent. Various embodiments described herein further describe devices and methods for deploying the valve leaflet prosthesis and stent assembly.

In various embodiments, the replacement heart valve leaflet prosthesis may include a shaped wire frame over which a flexible biocompatible panel or two-ply panel is sewn or otherwise secured. According to various embodiments, a single wire integral with the frame may extend as a tether wire (or "leg" or tether strut), which is pivotally coupled to a gimbal or other pivotal support structure disposed on an expandable anchoring stent. Thus, the various valve leaflet prostheses may be specifically configured to rotate in relation to the fixed anchoring stents.

Various embodiments of the stents employed may take numerous configurations independently useful for interventional cardiology, though structures may include features that enable the above-indicated pivotal coupling mechanism. According to various embodiments, the stent and valve leaflet prosthesis structures are each compressible to a small diameter for front loading into a catheter for percutaneous delivery to a patient's heart. The valve leaflet prostheses and stents are mechanically maintained in the compressed configuration and then allowed to expand once properly positioned at the intended target site. According to various embodiments, the delivery system may also enable full retrieval and/or partial retrieval for rotation or other kinds of repositioning of the stents if adjustments to anchoring are needed to ensure optimal replacement valve function. As will be appreciated, the stents and prosthesis wire (or the wire frame of the valve leaflet prosthesis) are preferably fabricated from a shape memory material, such as nitinol or another shape memory alloy.

In various embodiments, the delivery system is an over-the-wire ("OTW") system that provides a method to deliver the stent and the valve leaflet prosthesis into a tricuspid valve. The delivery system may include a handle having two deployment knobs, an outer sheath (which constrains the stent and valve leaflet prosthesis), an inner catheter (which is a stent carriage and prosthesis holder), and a nosecone with a guidewire slot (mounted on a separate component allowing limited distal movement). In various embodiments, the handle may include discrete controls for the valve leaflet prosthesis and stent components of the system. According to various embodiments, the handle may come in various configurations common to the medical device environment, including a deflectable distal sheath tip, which is activated by a handle control. Although the embodiments depicted in the drawings do not illustrate this specific configuration, it may be incorporated into the device and procedure.

The following examples pertain to various embodiments.

Example 1 is a valve implant including:
  a valve leaflet prosthesis having a wire frame, a leaflet blade panel attached to the wire frame, and one or more tether struts extending from the wire frame; and
  a stent having a first end portion and a second end portion along a longitudinal stent axis, and a flexible extended stent strut extending longitudinally from the first end portion,
  wherein the one or more tether struts of the valve leaflet prosthesis are rotatably coupled to the flexible extended stent strut in a manner such that the one or more tether struts are rotatable about a rotational axis which is parallel to the one or more tether struts and which extends transverse to the longitudinal stent axis.

In Example 2, the subject matter of Example 1 may optionally include a cylindrical coupling member having a longitudinal cylinder axis and connecting the one or more tether struts of the valve leaflet prosthesis to a connection portion of the flexible extended stent strut, wherein the one or more tether struts are inserted into the cylindrical coupling member in a manner so as to be parallel to the longitudinal cylinder axis of the cylindrical coupling member, and wherein the connection portion of the flexible extended stent strut is in a rotational engagement with the cylindrical coupling member such that the longitudinal cylinder axis of the cylindrical coupling member defines the rotational axis.

In Example 3, the subject matter of Example 2 may optionally include that the cylindrical coupling member may have a continuous endless circumferential groove around an exterior cylindrical surface thereof, wherein the connection portion of the flexible extended stent strut includes a loop which is engaged with the continuous endless circumferential groove of the cylindrical coupling member in a manner such that the cylindrical coupling member is rotatable relative to the loop about the longitudinal cylinder axis of the cylindrical coupling member.

In Example 4, the subject matter of Example 3 may optionally include that the loop may be formed by a hook, the hook may include a shank portion having a sinuous profile, followed by a bend portion, and followed by a finger portion extending alongside the shank portion in a manner so as to form a sinuous capturing slot between the shank portion and the finger portion.

In Example 5, the subject matter of Example 4 may optionally include that the shank portion may have at least one lobe extending towards the finger portion and the finger portion may have at least one lobe extending towards the shank portion, wherein the at least one lobe of the shank portion juts over the at least one lobe of the finger portion in an overhanging manner so as to form the sinuous capturing slot meandering around the at least one lobe of the shank portion and the at least one lobe of the finger portion.

In Example 6, the subject matter of any one of Examples 2 to 5 may optionally include that the cylindrical coupling member may include a circular cross-section, or an oval cross-section, or an elliptic cross-section.

In Example 7, the subject matter of any one of Examples 1 to 6 may optionally include that the leaflet blade panel may include a layered arrangement of two or more layers, and wherein a first layer has a perimeter border wider than a perimeter border of a second layer.

In Example 8, the subject matter of any one of Examples 1 to 7 may optionally include that the valve leaflet prosthesis may include a guide hole arrangement at a leaflet-tip-portion of the valve leaflet prosthesis.

In Example 9, the subject matter of Example 8 may optionally include that the guide hole arrangement may include a guide hole through the leaflet blade panel of the valve leaflet prosthesis, or a bead which is coupled to the wire frame and which has a guide hole through the bead.

Example 10 is a delivery system for the valve implant according to any one of Examples 1 to 9, the delivery system including:
  a delivery device including
    an outer sheath,
    an inner catheter inserted into the outer sheath in a manner so as to be slidable relative to the outer sheath, wherein the inner catheter has a guidewire lumen extending throughout an entire length of the inner catheter and includes a stent carrier arrangement at an end portion of the inner catheter,
    a nosecone assembly having a nosecone-rod extending longitudinally from an end of the inner catheter and a nosecone disposed at an end of the nosecone-rod, wherein the nosecone includes a leaflet-prosthesis-alignment-element, and
    a guidewire insertion tool extending longitudinally and coaxially from an end of the guidewire lumen of the inner catheter so as to serve as a continuation of the guidewire lumen; and
  the valve implant according to any one of Examples 1 to 9,
  wherein the stent of the valve implant is compressed to wrap around the stent carrier arrangement, the flexible extended stent strut is bent so as to align the one or more tether struts of the valve leaflet prosthesis longitudinally with respect to the stent, and the valve leaflet prosthesis of the valve implant is compressed into an elongate shape and placed in engagement with the leaflet-prosthesis-alignment-element of the nosecone.

In Example 11, the subject matter of Example 10 may optionally include that the stent of the valve implant may include a movement-restraining-engagement element and the stent carrier arrangement of the inner catheter may include a corresponding movement-restraining-engagement element, wherein the movement-restraining-engagement element of the stent engages with the corresponding movement-restraining-engagement element of the stent carrier arrangement when the stent is compressed and wrapped around the stent carrier arrangement in a manner so as to restrict relative movement between the stent and the stent carrier arrangement.

In Example 12, the subject matter of Example 11 may optionally include that the movement-restraining-engagement element of the stent may include a hook or a notch and the corresponding movement-restraining-engagement element of the stent carrier arrangement may include correspondingly shaped protrusions, or wherein the movement-restraining-engagement element of the stent may include shaped extension and the corresponding movement-restraining-engagement element of the stent carrier arrangement may include correspondingly shaped recesses.

In Example 13, the subject matter of any one of Examples 10 to 12 may optionally include a control handle coupled to the delivery device, the control handle including
  a first control mechanism configured to control and actuate the inner catheter to move axially relative to the outer sheath; and
  a second control mechanism configured to control and actuate the outer sheath to move axially relative to the inner catheter.

In Example 14, the subject matter of any one of Examples 10 to 13 in combination with the valve implant according to Example 8 or 9 may optionally include that the guidewire insertion tool may be inserted through the guide hole arrangement of the valve leaflet prosthesis.

Example 15 is a method of preparing the delivery system of any one of Examples 10 to 14 for delivering the valve implant of any one of Examples 1 to 9, the method including:
  inserting a guidewire, in a front loading manner, through the guidewire insertion tool and through the guidewire lumen of the inner catheter; and
  removing the guidewire insertion tool from the delivery system such that the guidewire remains inserted through the guidewire lumen of the inner catheter.

Example 16 is a method of implanting the valve leaflet implant of Example 6 or 9 in valve repair procedure for tricuspid regurgitation using the delivery system of Example 15, the method including:
  directing a first end of a guidewire via inferior vena cava access through a right atrium of the heart and into a right ventricle of the heart such that a final segment of the guidewire curves from the inferior vena cava, through the right atrium and into the right ventricle;
  inserting a second end of the guidewire in to the delivery system, in a front loading manner, through the guidewire insertion tool and through the guidewire lumen of the inner catheter;
  removing the guidewire insertion tool from the delivery system such that the guidewire remains inserted through the guide hole arrangement of the valve leaflet prosthesis and through the guidewire lumen of the inner catheter;
  advancing the delivery system along the guidewire until the nosecone is at a transition region between the inferior vena cava and the right atrium;
  advancing the inner catheter relative to the outer sheath in a manner such that, as the nosecone advance away from a corresponding end of the outer sheath in a straight path, the valve leaflet prosthesis dislodges from the leaflet-prosthesis-alignment-element of the nosecone, expands into an original shape and continue to advance along the final segment of the guidewire curving into the right ventricle in a manner so as to be positioned alongside native tricuspid leaflets of the heart;
  retracting the outer sheath relative to the inner catheter in a manner such that, as the outer sheath retreats to expose the stent, the stent expands and dislodges from the stent carrier arrangement in a manner so as to be anchored to the inferior vena cava; and
  withdrawing the guidewire and the delivery system.

In Example 17, the subject matter of Example 16 may optionally include measuring a diameter of the inferior vena cava;
measuring a distance between a tip of the tricuspid leaflets of the heart to a closest edge of the inferior vena cava;
selecting the stent based on the measured diameter of the inferior vena cava;
selecting the valve leaflet prosthesis based on the measured distance between the tip of the tricuspid leaflets of the heart to the closest edge of the inferior vena cava;
assembling the stent and the valve leaflet prosthesis to form the valve implant;
loading the valve implant onto the delivery device.

Referring to FIG. 1 through FIG. 13D, wherein like reference numerals refer to like components in the various views, there is illustrated therein an embodiment of a valve leaflet prosthesis and stent assembly (or a valve implant or a valve replacement assembly or a replacement valve), together with an embodiment of a delivery device. According to various embodiments, a delivery system may include the valve implant and the delivery device.

Turning first to FIGS. 1-6 there is shown a delivery device 10 having an anchoring stent 12 (or a stent) and a valve leaflet prosthesis (with only a wire frame 14a of the valve leaflet prosthesis shown) loaded for delivery. Accordingly, the delivery device 10, the stent 12 and the valve leaflet prosthesis together may form a delivery system 1. According to various embodiments, the valve leaflet prosthesis may include the wire frame 14a and a leaflet blade panel attached to the wire frame 14a. According to various embodiments, the stent 12 may include a first end portion and a second end portion along a longitudinal stent axis. As shown in the figures, the delivery device 10 includes an inner catheter 16 and an outer sheath 18 axially and slidingly disposed over the inner catheter 16. Medially the delivery device 10 includes a cylindrical stent carrier 20 (or a stent carrier arrangement) integral with and disposed distally of the inner catheter 16 and having an integral proximal collar 22 and a distal collar 24. The distal collar 24 includes a longitudinally oriented channel 26. The channel 26 is a longitudinal cut along a cylindrical surface of the distal collar 24 to form a recess 25 with increasing depth so as to curve inwards, originating from the proximal end of the distal collar 24, in a manner such that the channel 26 ends with a small pocket.

At a proximal end 28, the delivery system includes a nosecone rod 30 and a guidewire lumen 32 extending from the inner catheter 16 (handle not shown). The nosecone rod 30 and guidewire lumen 32 extend distally from the inner catheter 16, and at a distal end 34, the nosecone rod 30 connects to a tapered nosecone 36 having a longitudinal slot 38 into which a guidewire insertion tool 40 is disposed. The guidewire insertion tool 40 connects to a distal end 42 of the guidewire lumen 32. The nosecone 36 includes an integral prosthesis alignment surface 44 (or a leaflet-prosthesis-alignment-element) having a hemispherical recess 46. According to various embodiments, the nosecone rod 30 and the nosecone 36 together forms a nosecone assembly 31. According to various embodiments, the guidewire lumen 32 extends throughout an entire length of the inner catheter 16. According to various embodiments, the guidewire insertion tool 40 extends longitudinally and coaxially from an end of the guidewire lumen 32 of the inner catheter 16 so as to serve as a continuation of the guidewire lumen 32.

Figure 2A:
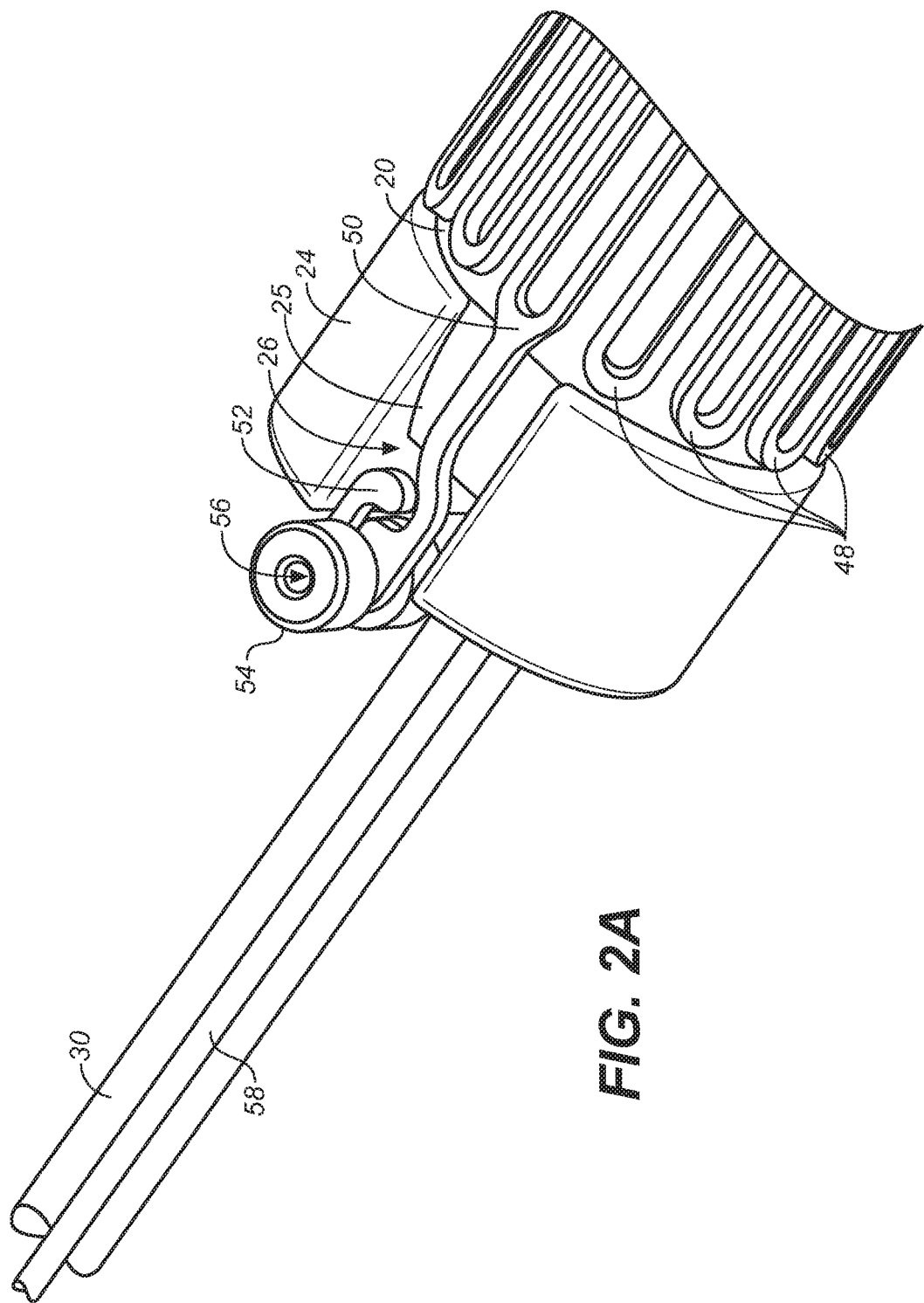
FIG. 2A is a detailed perspective view of a coupling gimbal (or a cylindrical coupling member) installed on a wire extension (or a flexible extended stent strut) of the stent of FIG. 1, as taken from circular broken line 2-2 of FIG. 1, according to various embodiments.
Figure 2B:
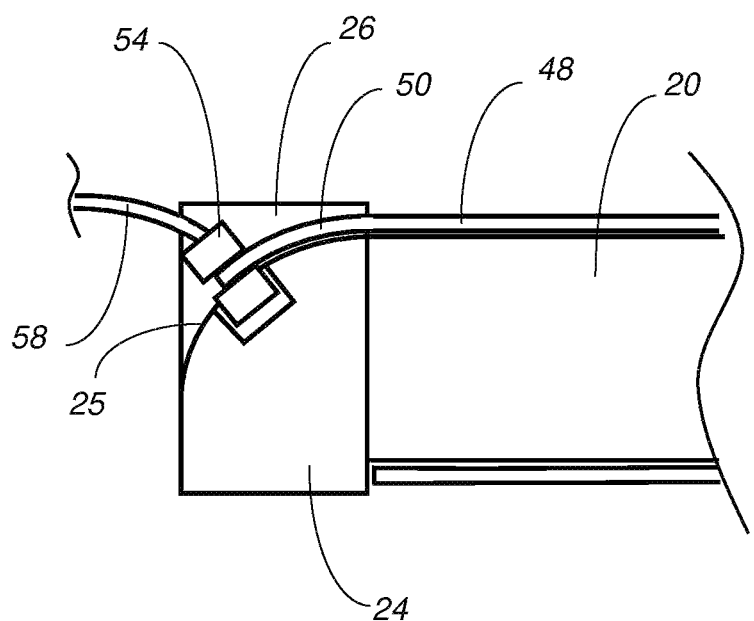
FIG. 2B is a schematic cross-sectional view of the coupling gimbal (or the cylindrical coupling member) fitted in a slot of a stent carrier arrangement of the delivery system of FIG. 1 according to various embodiments.

Looking now at FIG. 2A, the stent 12 includes a plurality of superelastic expandable shape memory alloy stent struts 48, one of which (or at least one flexible extended stent strut 50), extending longitudinally from the first end portion of the stent 12, includes an extended leg and integral hook 52 (or a loop or a connection portion) to capture and retain a gimbal 54 (or a cylindrical coupling member). The gimbal 54 may be cylindrical. The gimbal 54 may have a circular cross-section. The gimbal 54 includes a partially hollow axle 56 into which a wire tether 58 (or a tether strut) of the valve leaflet prosthesis is inserted (see FIG. 2B, note: in FIG. 1, FIG. 2A and FIG. 3, the wire tether 58 is illustrated without being inserted into the hollow axle 56). The wire tether 58 is integral with the wire frame 14a of the valve leaflet prosthesis (or the wire tether 58 extends from the wire frame 14a). Accordingly, when assembled, the wire tether 58 passes through a passage in a frame connector 60 and terminates in the hollow end of the gimbal axle 56. The wire tether 58 is allowed to rotate within the passage. The other end 62 of the wire frame 14a is also captured and terminates in the frame connector 60, but it is bonded and prevented from rotating in relation to the frame connector 60. The wire frame 14a is thereby formed in part by the conjunction of the proximal portion 64 of the wire frame 14a, and is also prevented from distorting into a folded configuration rather than generally planar configuration on deployment. According to various embodiments, the wire tether 58 may be inserted into the gimbal 54 in a manner so as to be parallel to a longitudinal cylinder axis of the cylindrical gimbal 54. The hook 52 may be in rotational engagement with the gimbal 54 such that the longitudinal cylinder axis of the cylindrical gimbal 54 defines the rotational axis (which is perpendicular to a surface of the hook 52 into which the gimbal 54 is inserted).

On a distal side 66, essentially in an opposing position relative to the frame connector 60, a spherical bead 68 is slidingly and rotatingly disposed on the wire frame 14a. The bead 68 includes two through holes oriented generally normal to one another, a first through hole 70 which allows passage of the wire frame 14a, and a second through hole 72 which allows passage of the guidewire insertion tool 40 and guidewire (not shown). According to various embodiments, the bead 68 may be a guide hole arrangement for sliding engagement with the guidewire insertion tool 40 and/or the guidewire, wherein the guide hole arrangement may be disposed at a leaflet-tip-portion of the valve leaflet prosthesis. Accordingly, the bead 68 is coupled to the wire frame 14a at the leaflet-tip-portion of the valve leaflet prosthesis and the bead 68 has the second through hole 72 (or the guide hole) for the guidewire insertion tool 40 and/or the guidewire to string through.

Figure 5:
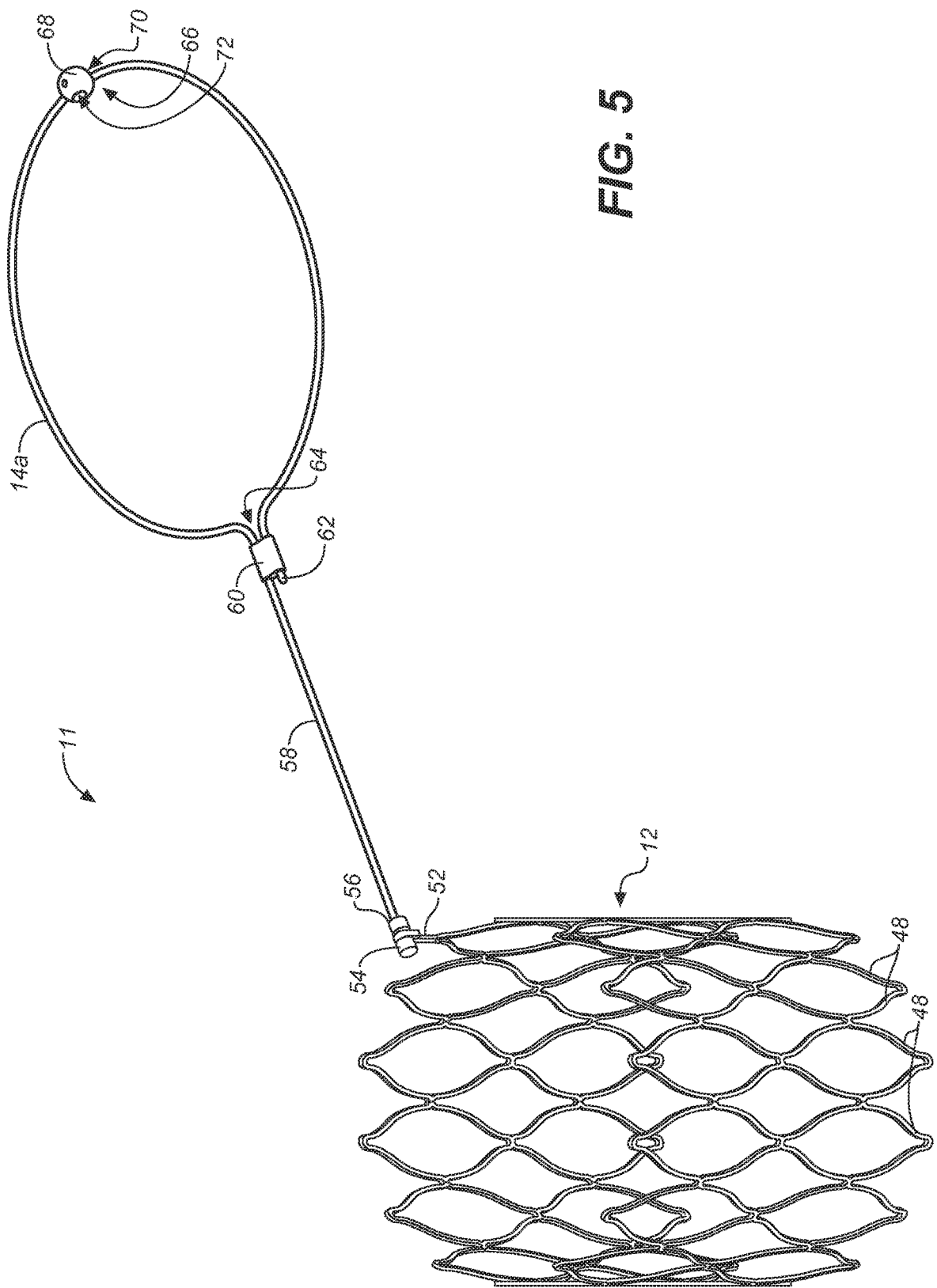
FIG. 5 is a perspective view of an embodiment of a stent coupled to a wire frame of a valve leaflet prosthesis according to various embodiments.

Turning next to FIG. 5, there is shown the pivotally coupled anchoring stent 12 and prosthesis wire frame 14a. According to various embodiments, a valve implant 11 (or a valve replacement assembly or a replacement valve) may include the stent 12 and the valve leaflet prosthesis (as represented by the prosthesis wire frame 14a in FIG. 5). FIG. 5 shows the valve implant 11 in fully deployed (expanded) configurations. As can be seen, when in the deployed state, the wire tether 58 (or the tether strut) of the valve leaflet prosthesis is in an approximately perpendicular orientation in relation to the side of the stent 12. The plane of the wire frame 14a may rotate due to gimbal rotation within the hook 52. According to various embodiments, the wire tether 58 of the valve leaflet prosthesis may be rotatably coupled to the flexible extended stent strut 50 in a manner such that the wire tether 58 may be rotatable about a rotational axis which is a longitudinal axis of the wire tether 58 (or which is parallel to the wire tether 58) and which extends transverse to the longitudinal stent axis (or is perpendicular to the surface of the hook 52 of the flexible extended stent strut 50 into which the gimbal 54 is inserted)

Figure 6A:
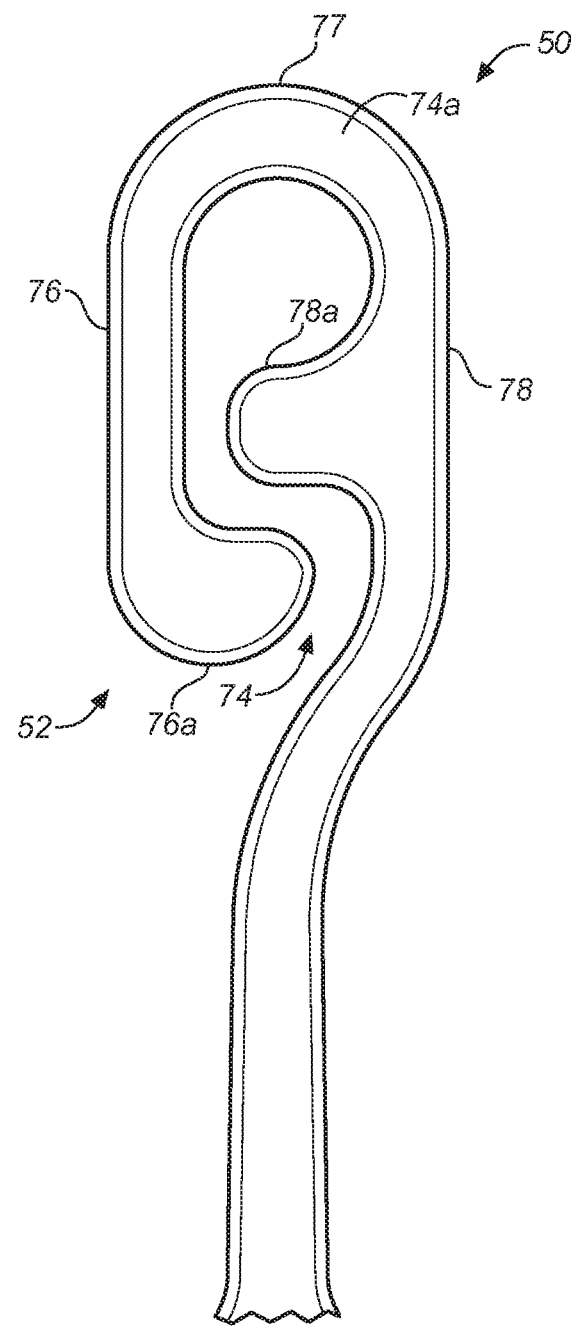
FIG. 6A is a plan view of a wire hook (or the extended stent strut) extending from the stent of the valve leaflet prosthesis of FIG. 5 according to various embodiments.
Figure 6B:
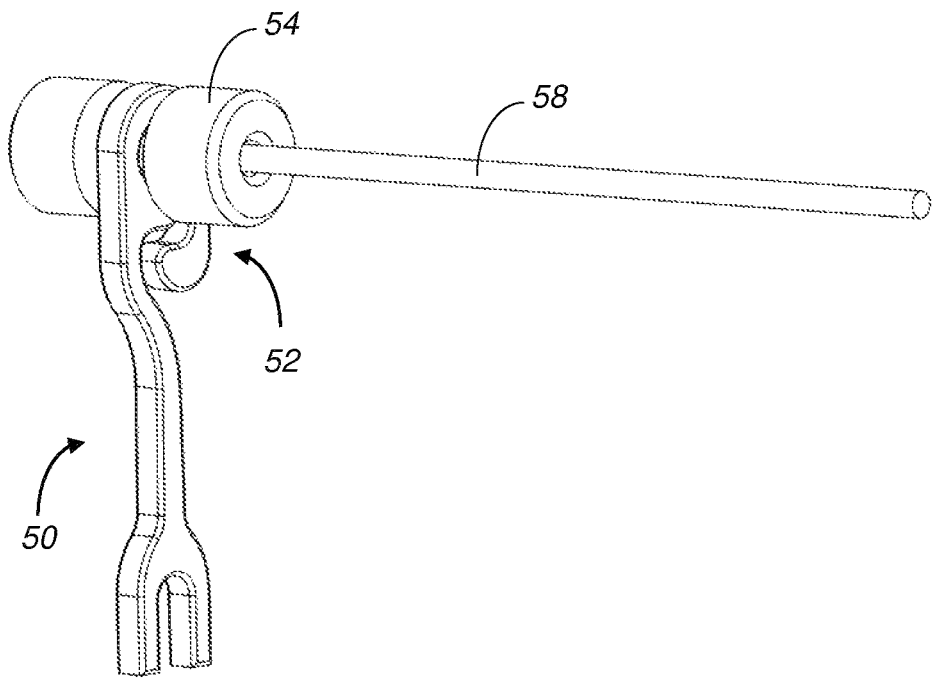
FIG. 6B is an assembly of the gimbal and the hook of FIG. 6A according to various embodiments.
Figure 6C:
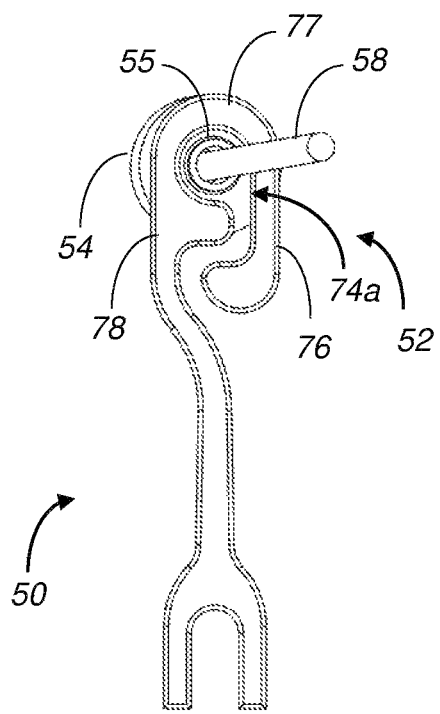
FIG. 6C is a right side view of FIG. 6B with part of the gimbal cut away to show detail of the fitting between the hook and the gimbal according to various embodiments.

FIG. 6A shows detail of the sinuous capturing slot 74 of the hook 52. FIG. 6B shows the gimbal 54 inserted into the hook 52. FIG. 6C shows a right side view of FIG. 6B with part of the gimbal 54 cut away to show detail of the fitting between the hook 52 and the gimbal 54. The capturing slot 74 is configured with a resilient nitinol finger portion 76 which defines an opening with respect to a shank portion 78, the opening sized to allow assembly in the sterile field and the free rotation of the gimbal 54 while also preventing egress of the gimbal 54 under blood flow forces encountered in situ. According to various embodiments, the gimbal 54 (or the cylindrical coupling member) may be cylindrical and may have a continuous endless circumferential groove 55 around an exterior cylindrical surface thereof. The hook 52 (or the connection portion of the flexible extended stent strut 50) may be engaged with the continuous endless circumferential groove 55 of the gimbal 54 in a manner such that the gimbal 54 is rotatable relative to the hook 52 about the longitudinal cylinder axis of the cylindrical gimbal 54. According to various embodiments, the hook 52 and the continuous endless circumferential groove 55 of the gimbal 54 may have a loose running clearance fit (see FIG. 6C) such that an opening of an open loop 74a formed by the hook 52 is of a larger diameter than a diameter of the continuous endless circumferential groove 55 of the gimbal 54. Accordingly, the gimbal 54 may be free to rotate about its longitudinal cylinder axis, and may further rock and tilt within the hook 52 such that the wire tether 58 may have some leeway to tilt in various directions with respect the hook 52. According to various embodiments, the loose running clearance fit between the hook 52 and the continuous endless circumferential groove 55 of the gimbal 54 may configured to allow a tilting movement of the gimbal 54 and the wire tether 58 of a range of 0° to 45°. According to various embodiments, the hook 52 may include the shank portion 78 having a sinuous profile, followed by a bend portion 77, and followed by the finger portion 76 extending alongside the shank portion 78 in a manner so as to form a sinuous capturing slot between the shank portion 78 and the finger portion 76. According to various embodiments, the shank portion 78 may have at least one lobe 78a extending towards the finger portion 76 and the finger portion may have at least one lobe 76a extending towards the shank portion 78. The at least one lobe 78a of the shank portion 78 may jut over the at least one lobe 76a of the finger portion 76 in an overhanging manner so as to form the sinuous capturing slot 74 meandering around the at least one lobe 78a of the shank portion 78 and the at least one lobe 76a of the finger portion 76.

FIGS. 7A through 8B show various valve leaflet prosthesis 80, 90, 92, 96 configurations according to various embodiments. Each configuration shown is a two-ply fabric panel sewn or welded onto the above-described prosthesis wire frame 14a. This configuration also allows a single-layer fabric panel. According to various embodiments, the two-ply fabric panel and/or the single-layer fabric panel may form the respective leaflet blade panel 14b of the respective valve leaflet prosthesis 80, 90, 92, 96. In an embodiment (FIG. 7A), the valve leaflet prosthesis 80 may include first and second generally triangular panels, 82, 84, sewn or welded at the wire frame 14a, the bonding also capturing the spherical bead 68. The first panel 82 may include a perimeter border 86 slightly wider than the perimeter border 88 on the second panel 84. Accordingly, the leaflet blade panel of the valve leaflet prosthesis may include a layered arrangement of two or more layers wherein a first layer has a perimeter border wider than a perimeter border of a second layer. This enables the borders 86, 88 to work independently in providing an improved seal at the valve site. In a second embodiment (FIG. 7B), the same operational features may be incorporated in an oval valve leaflet prosthesis 90.

In other embodiments, triangular valve leaflet prosthesis 92 (FIG. 8A) and oval valve leaflet prosthesis 96 (FIG. 8B), the perimeter borders 94, 98, respectively, are coincident.

Figure 9:
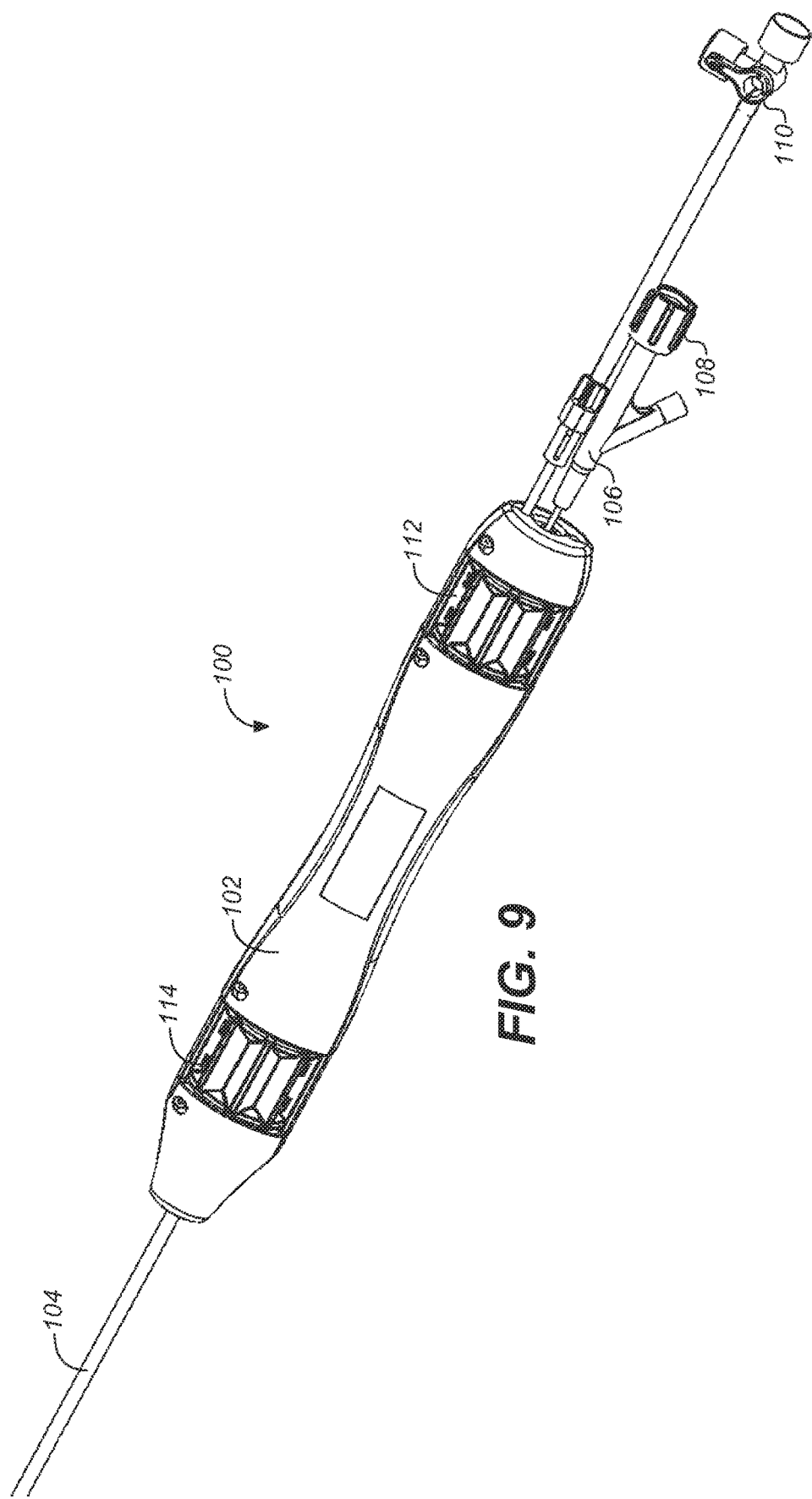
FIG. 9 is a perspective view of a control device adapted for use with the delivery system of FIG. 1 according to various embodiments.
Figure 11A:
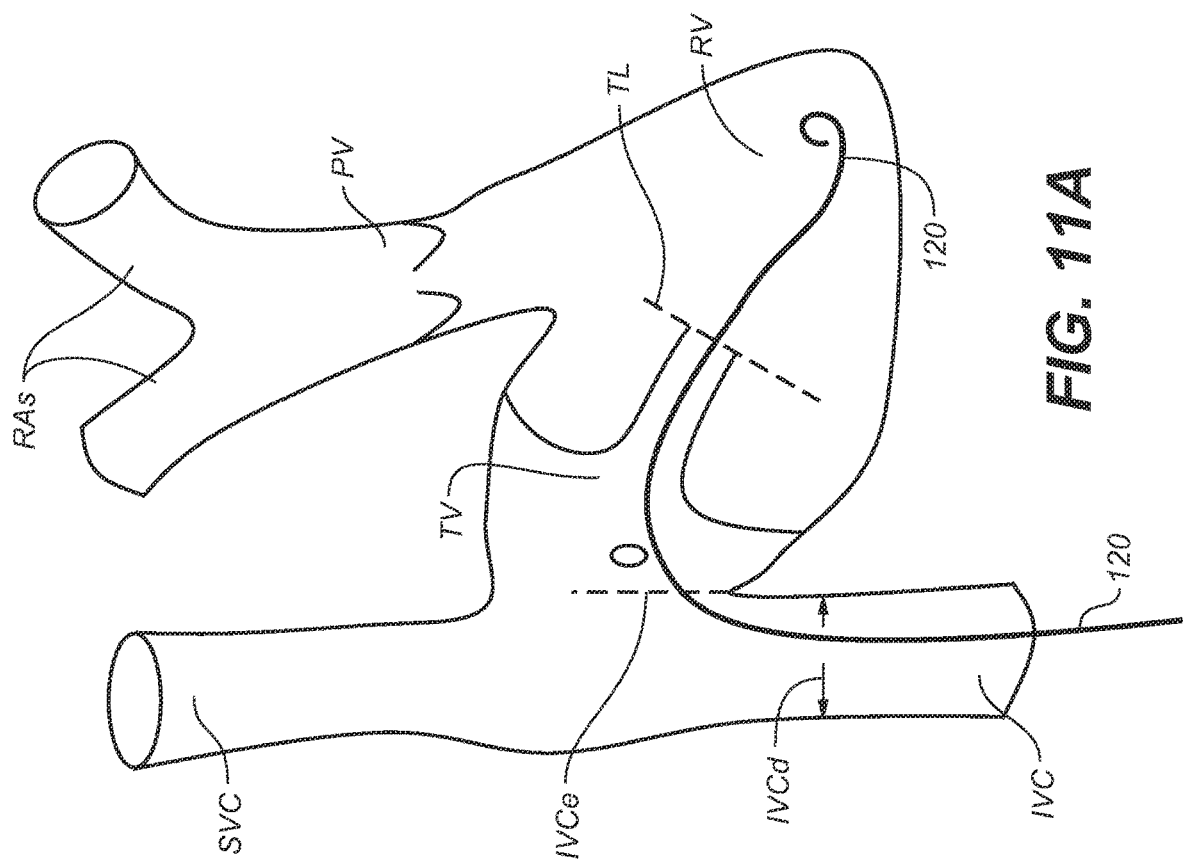
FIG. 11A is a schematic view showing the first steps for delivering the stent and the valve leaflet prosthesis in a human heart, this view showing the process for measuring the distance from a tricuspid leaflet edge to the inferior vena cava edge, as well as the IVC diameter, according to various embodiments.

FIG. 9 shows a control device 100 (or a control handle or a control) adapted for use with the delivery system of the various embodiments. The control device 100 includes a housing 102 shaped for gripping, a tubular member 104 (i.e. outer sheath 18) extending distally encloses the inner catheter 16 containing the guidewire lumen 32 of the delivery and nosecone rod 30, a proximal guidewire lumen 106 having a homeostasis valve 108, and a flush port 110. Rotatable control rings 112, 114 (or first and second control mechanisms) are, respectively, directed to extension and retraction of the valve leaflet prosthesis and the outer sheath 18 covering the expandable stent 12. According to various embodiments, the first rotatable control ring 112 (or the first control mechanism) may be configured to control and actuate the inner catheter 16 to move axially relative to the outer sheath 18 so as to advance the valve leaflet prosthesis. According to various embodiments, the second rotatable control ring 114 (or the second control mechanism) may be configured to control and actuate the outer sheath 18 to move axially relative to the inner catheter 16 so as to retract the outer sheath 18 to expose the expandable stent 12.

Figure 10:
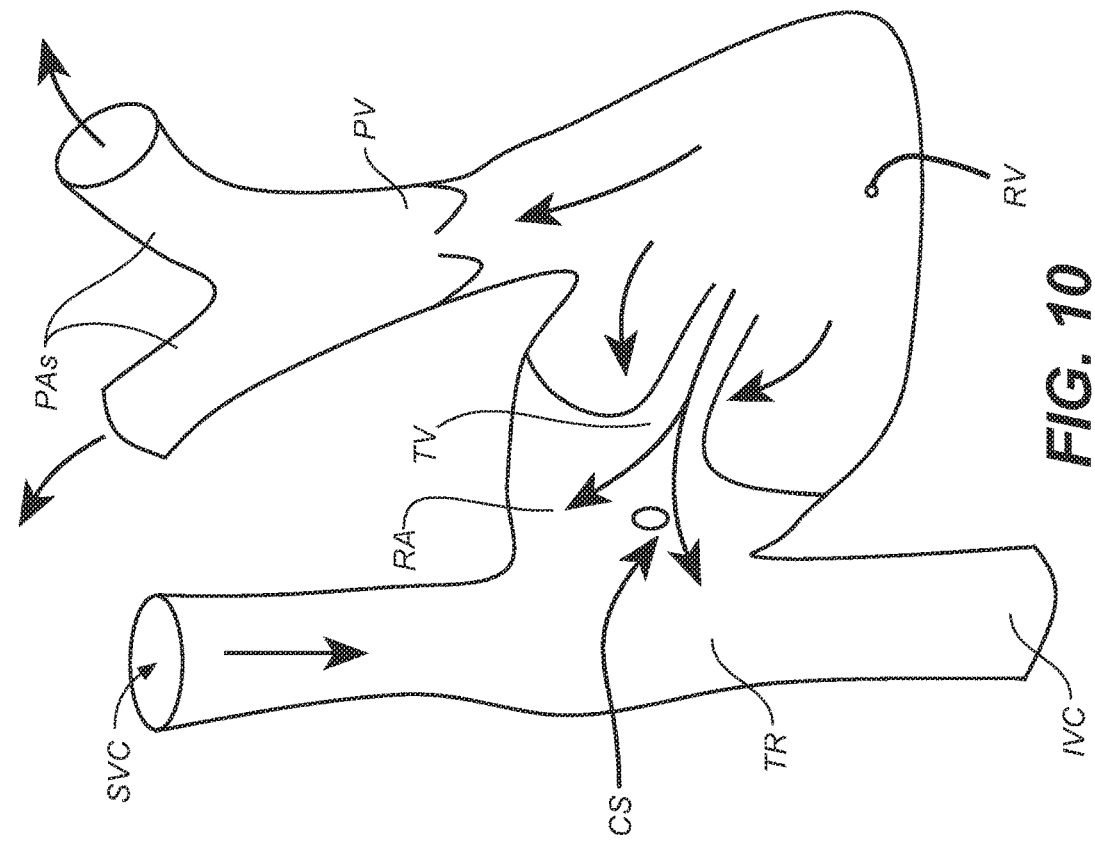
FIG. 10 is a highly schematic partial view of the human heart showing the inferior vena cava, the superior vena cava, the right atrium and the right ventricle, the pulmonary valve, and the pulmonary arteries.

Referring now to FIG. 10, there is shown in a highly schematic illustration how tricuspid regurgitation affects blood flow during the systole phase of the cardiac cycle. Upon right ventricle RV contraction, blood flows backwards through the tricuspid valve TV into the right atrium RA.

Turning next to FIGS. 11A-13D, in use, after a patient is prepped for surgery and stabilized, inferior vena cava (IVC) venous access is obtained and a suitable 0.035/0.038" guidewire 120 is directed into the right ventricle RV. Accordingly, a first end of the guidewire may be directed via inferior vena cava access through the right atrium RA of the heart and into the RV of the heart such that a final segment of the guidewire curves from the IVC, through the RA and into the RV. A radio opaque marker pigtail is then advanced into the RV and the distance from the bottom (or tip) of the tricuspid leaflet TL to the closest edge of the inferior vena cava IVCe is evaluated and measured using contrast injections and various C-Arm angles. This determines the valve leaflet prosthesis size. Accordingly, the valve leaflet prosthesis 14 is selected based on the measured distance.

Figure 11B:
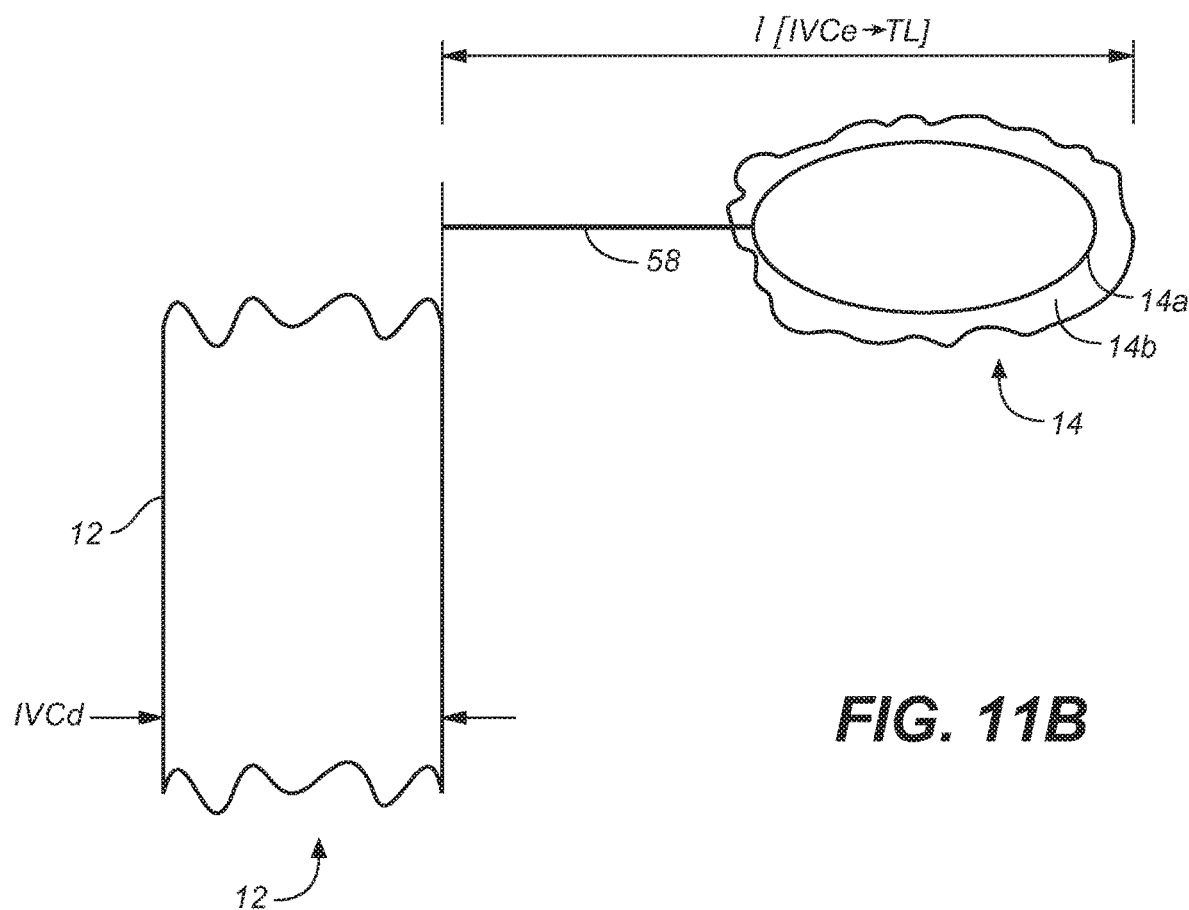
FIG. 11B is a schematic view showing how the measurements determine the valve leaflet prosthesis and stent sizes according to various embodiments.

Next, and referring to FIG. 11B, the IVC diameter IVCd is sized or measured under either fluoroscopy imaging or CT reconstruction. This determines the size of the IVC stent 12. Accordingly, the stent 12 is selected based on the measured diameter.

Figure 12A:
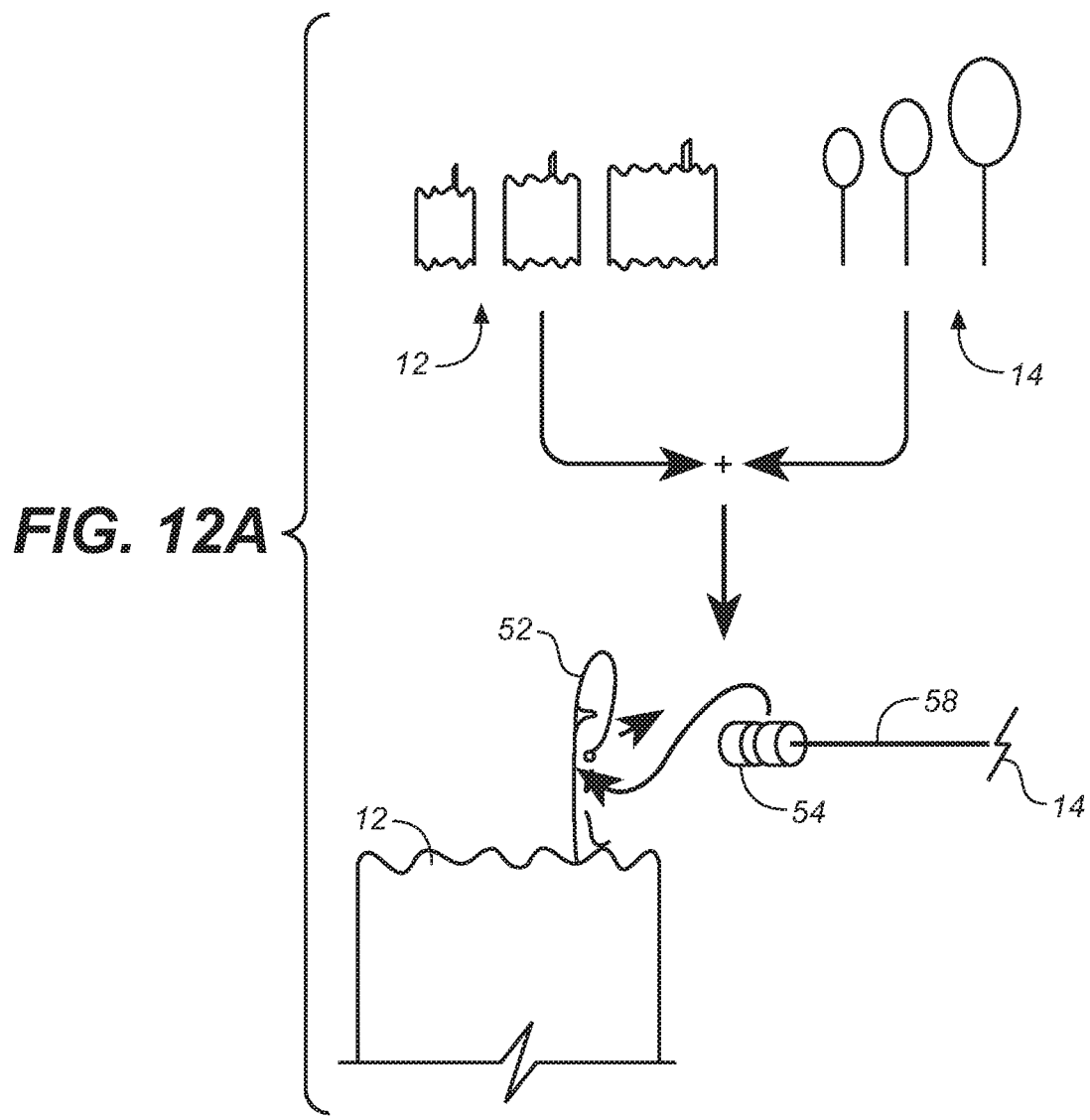
FIG. 12A is a schematic view showing the step of selecting an appropriately sized and shaped stent and valve leaflet prosthesis and coupling of the valve leaflet prosthesis tether wire to the coupling gimbal installed on the anchoring stent according to various embodiments.

Next, FIG. 12A, the sterile implant is prepared, first by choosing the appropriate sizes for the IVC stent 12 and the valve leaflet prosthesis 14 (or implant prosthesis). The valve leaflet prosthesis 14 permanently "clips" into the extended leg and hook 52 of the IVC stent 12 while expanded in iced saline. Accordingly, the selected valve leaflet prosthesis 14 and the selected stent 12 are assembled to form the valve implant. Note that the flexible extended stent strut 50 bends to allow loading. When it bends the gimbal moves into slot 26 [see also FIG. 2B]. Upon deployment, the extended stent strut 50 straightens and directs the valve leaflet prosthesis 14 into the RV.

Figure 12B:
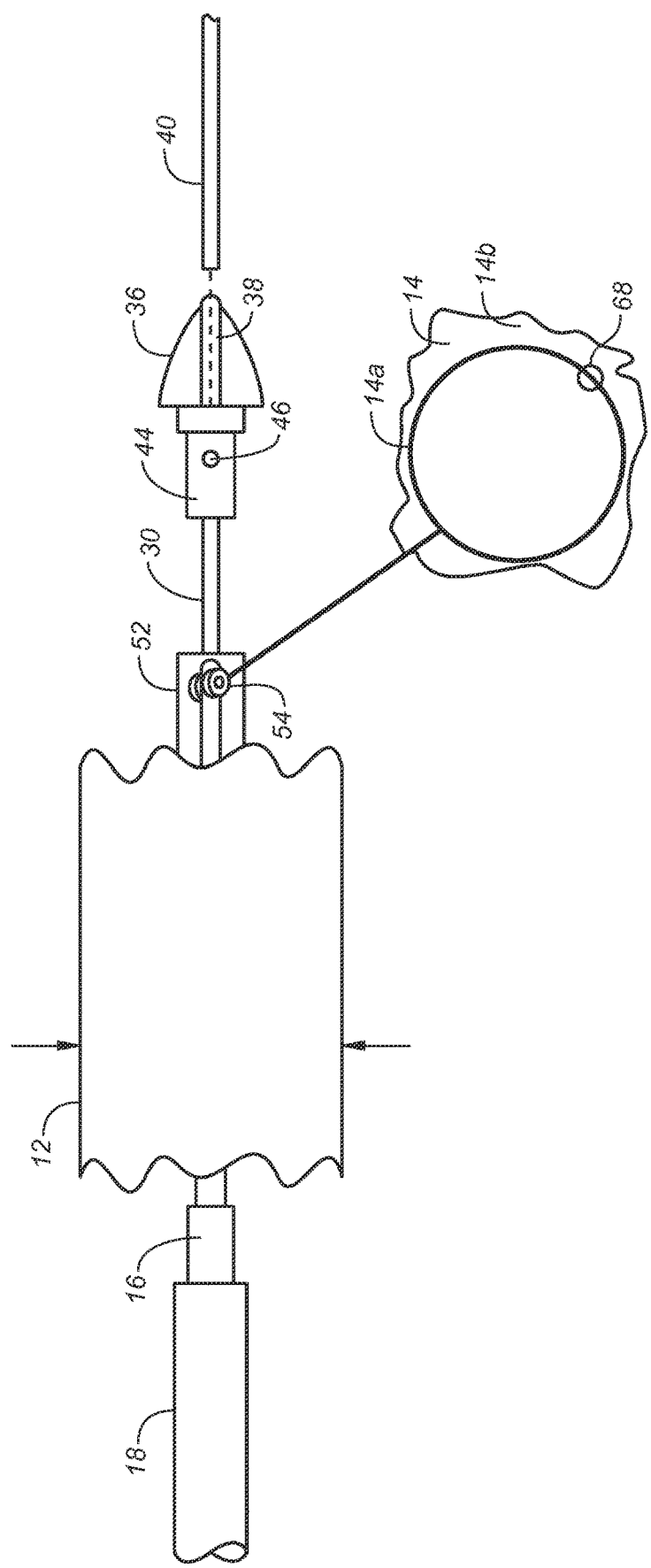
FIG. 12B is a schematic view showing how the stent and valve leaflet prosthesis are loaded into the delivery system according to various embodiments.

Next, FIG. 12B, the assembly—combined valve leaflet prosthesis 14 and stent 12—are loaded into the delivery system using a loading tool and iced saline. The stent 12 is compressed onto the stent carrier 20 using a crimp tool (such that the stent 12 wraps around the stent carrier 20), and the valve leaflet prosthesis 14 is also compressed and loaded onto the nosecone rod 30 with the spherical bead 68 disposed in the bead recess 46 (such that the valve leaflet prosthesis 14 is compressed into an elongate shape to place the leaflet-tip-portion of the valve leaflet prosthesis 14 with the spherical bead 68 in engagement with the prosthesis alignment surface 44, wherein the guidewire insertion tool 40 is inserted through the spherical bead 68). The gimbal 54 is then aligned with the nosecone slot 38 and the outer sheath 18 is advanced to secure the stent 12 and valve leaflet prosthesis 14 in compressed configurations. The system is then flushed. The guidewire is front loaded into the delivery system, and the guidewire insertion tool 40 is removed. Note that the guidewire loading tool 40 may be constructed from a single-sided split or dual-sided tear-away lumen with integral grasp tabs. According to various embodiments, the guidewire may be inserted in a front loading manner through the guidewire insertion tool 40 and through the guidewire lumen 32 of the inner catheter 16. Subsequently, the guidewire insertion tool 40 may be removed such that the guidewire remains inserted through the bead 68 and through the guidewire lumen 32 of the inner catheter 16.

Looking now at FIG. 13A, the delivery system is advanced to the RA, and using multiple C-Arm views, the IVC stent 12 is viewed and oriented such that the extended leg and hook 52 is angled toward the RV. Accordingly, the delivery system may be advanced along the guidewire until the nosecone is at a transition region between the IVC and the RA, or at the RA.

Figure 13B:
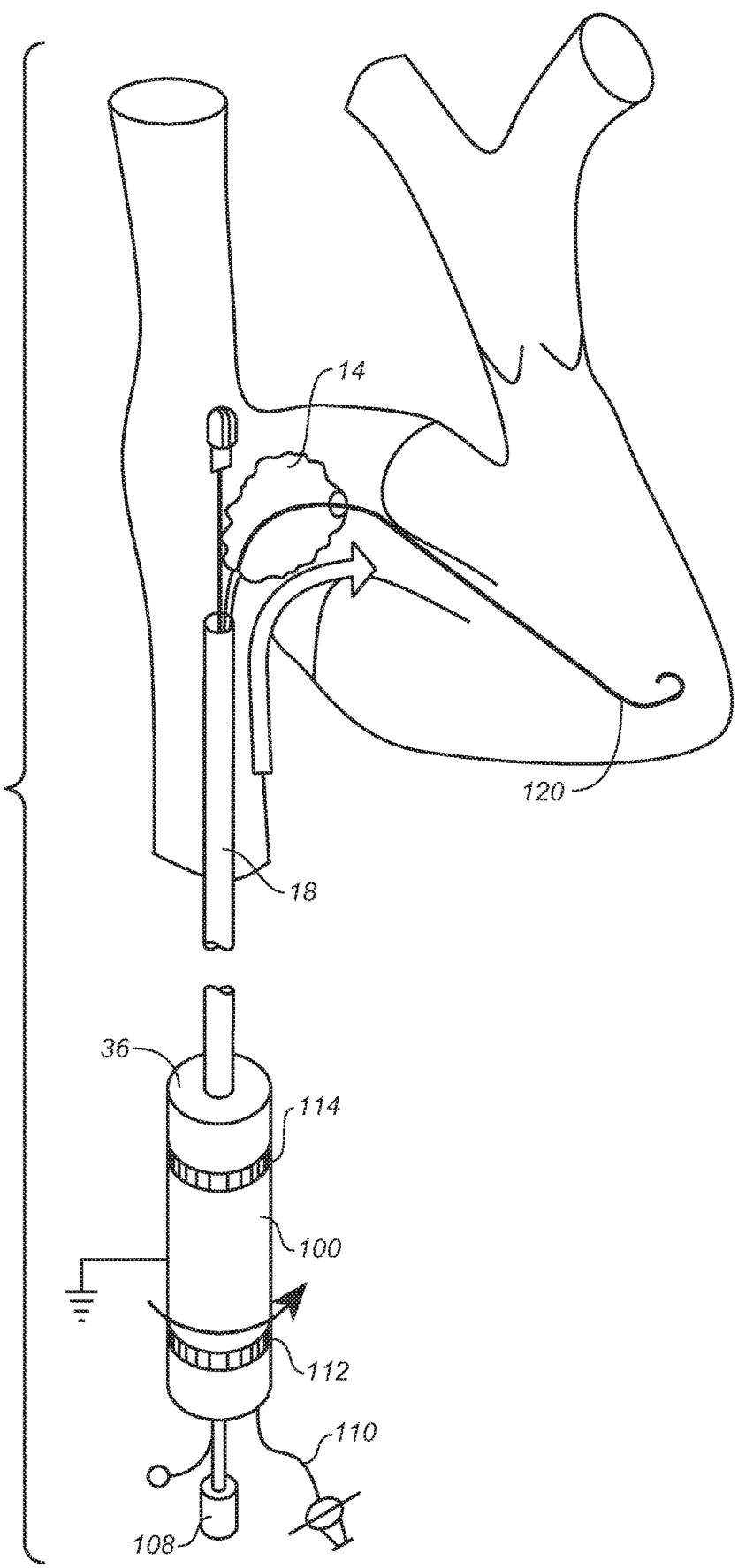
FIG. 13B is a schematic showing the deployment of the valve leaflet prosthesis into the RV according to various embodiments.

The valve leaflet prosthesis 14 is then deployed [FIG. 13B]. First, the handle is pinned to the patient table and the prosthesis deployment knob 112 on the control 100 [see FIG. 9] is rotated to unsheath and advance the valve leaflet prosthesis 14 (which follows the guidewire) while the nosecone 36 advances slightly into the RA. The nosecone 36 will advance only approximately 1 inch, due to a limiting feature in the handle 100, to prevent interaction with the RA and superior vena cava SVC. Accordingly, the inner catheter 16 may be advanced relative to the outer sheath 18 in a manner such that, as the nosecone 36 advance away from a corresponding end of the outer sheath 18 in a straight path, the valve leaflet prosthesis 14 dislodges from the prosthesis alignment surface 44 of the nosecone 36, expands into an original shape and continue to advance along the final segment of the guidewire curving into the RV in a manner so as to be positioned alongside native tricuspid leaflets of the heart.

At this point in the procedure, the clinician may observe residual tricuspid regurgitation TR under echocardiogram and adjust the valve leaflet prosthesis 14 position via the delivery system to determine the optimal result while positioning the delivery system to finalize the position of the IVC extended leg (or the flexible extended stent strut 50) and the gimbal 54. Once optimal results have been achieved via proper positioning, the control 100 remains pinned and its position maintained.

Figure 13C:
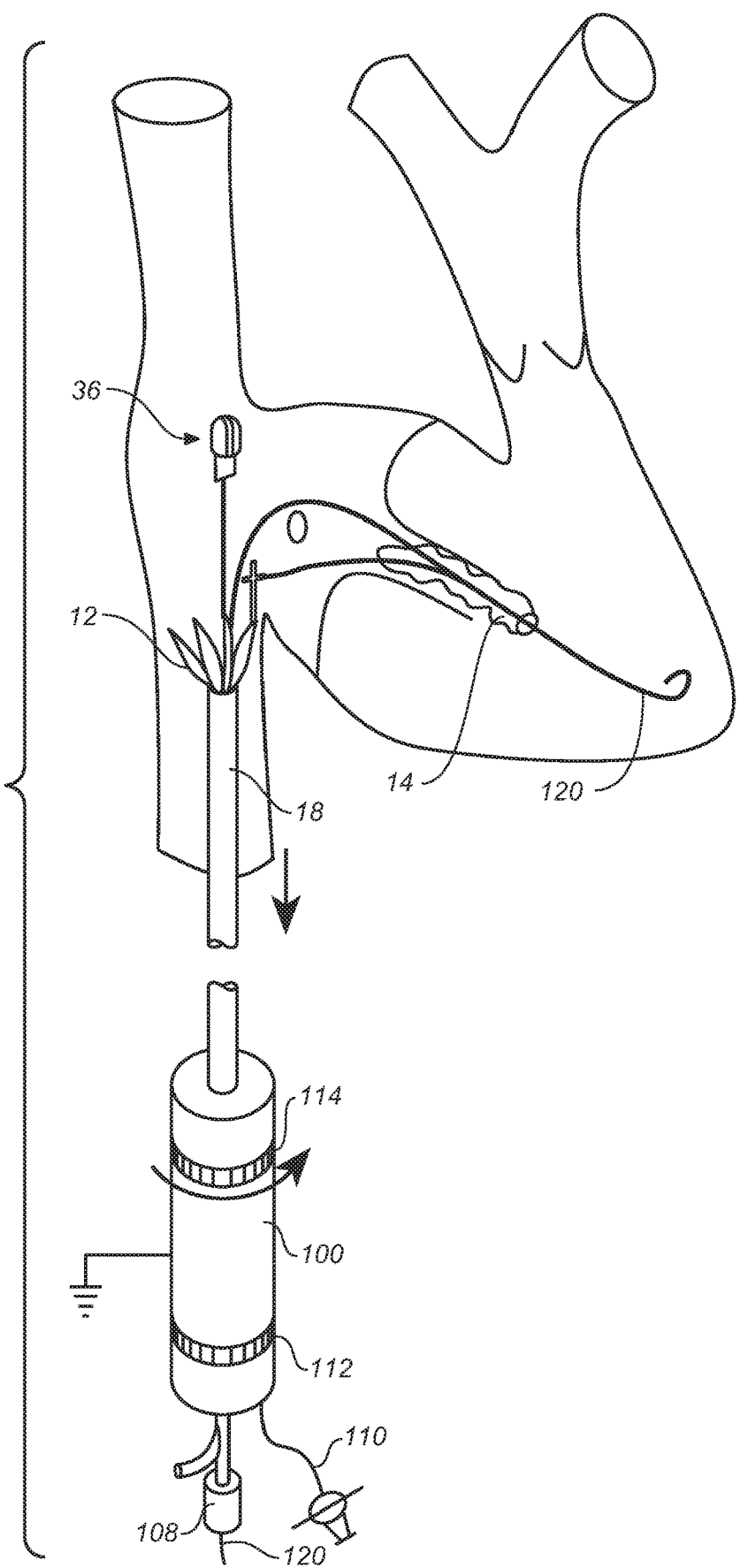
FIG. 13C is a similar view showing the deployment of an anchoring stent according to various embodiments.

The next step is stent deployment, FIG. 13C. To accomplish this, the control 100 is pinned to the patient table and the sheath deployment knob 114 for the stent 12 is rotated to unsheath the IVC stent 12. Adjustments may be made, such as advancing the delivery system slightly, to correct for any stent foreshortening. Hemodynamics are then evaluated using fluoroscopy or echocardiogram. Accordingly, the outer sheath 18 may be retracted relative to the inner catheter 16 in a manner such that, as the outer sheath 18 retreats to expose the stent 12, the stent 12 expands and dislodges from the stent carrier 20 in a manner so as to be anchored to the IVC.

Figure 13D:
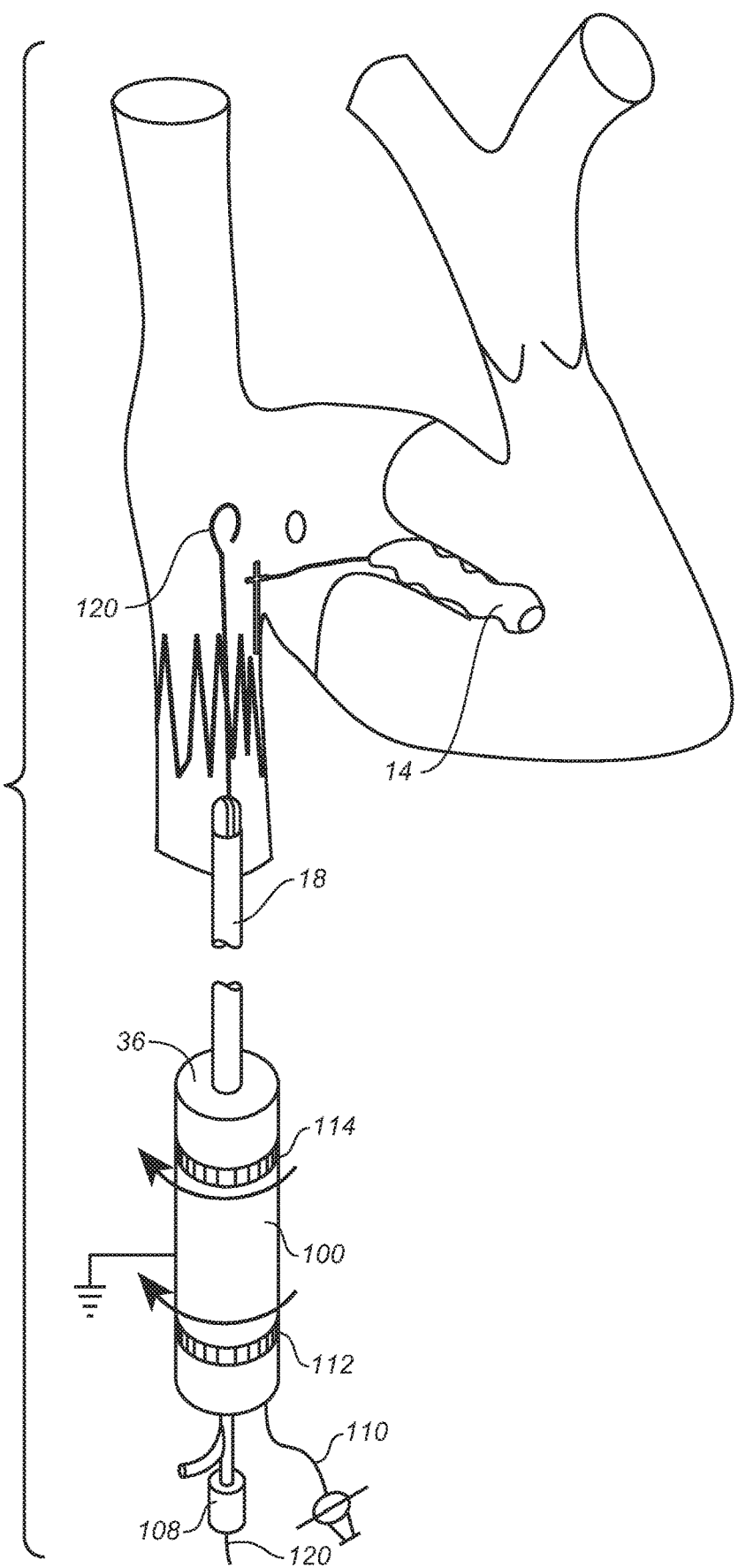
FIG. 13D is the same view showing removal of the delivery system after placement of the stent and valve leaflet prosthesis according to various embodiments.

Finally, and looking now at FIG. 13D, the delivery system is removed. Both deployment knobs 112, 114, are rotated back to their respective positions to advance the outer sheath 18 and to retract the nosecone 36. The delivery system and guidewire are then removed.

The various valve leaflet prosthesis 14 configurations illustrated offer distinct advantages in the ability to effectively seal the annulus due to the extension of the fabric (of the leaflet blade panel 14b) beyond the prosthesis Nitinol frame (or the wire frame 14a). This extended fabric allows blood flow to push it against the native leaflets and for the offset examples, provide a stiffness transition to control the apposition of the fabric against the native leaflet. This ultimately provides more benefit to the patient in reducing TR.

The separate components of the Nitinol stent 12 and valve leaflet prosthesis 14 provides the clinician the benefit of choosing the best combination to fit the patient's anatomy as well as reducing the number of components needed to stock in the hospital interventional suite. The manufacturing of the components is simplified due to being able to process them separately in lower risk operations thus making the device more cost efficient.

The procedural embodiment of the delivery system demonstrating a non-steerable sheath reduces cost and procedure time FIG. 1 through FIG. 13D provided illustrations of various embodiments. However, these embodiments do not limit the invention to the exact construction, dimensional relationships, and operation shown and described. Modifications, alternative constructions, changes and equivalents will readily occur to those skilled in the art and may be employed, as suitable. It will be understood that the various changes, modification, variation in form and detail described in the following may be combined with, adapted to, and/or incorporated into the various embodiments of FIG. 1 through FIG. 13D.

Figure 3:
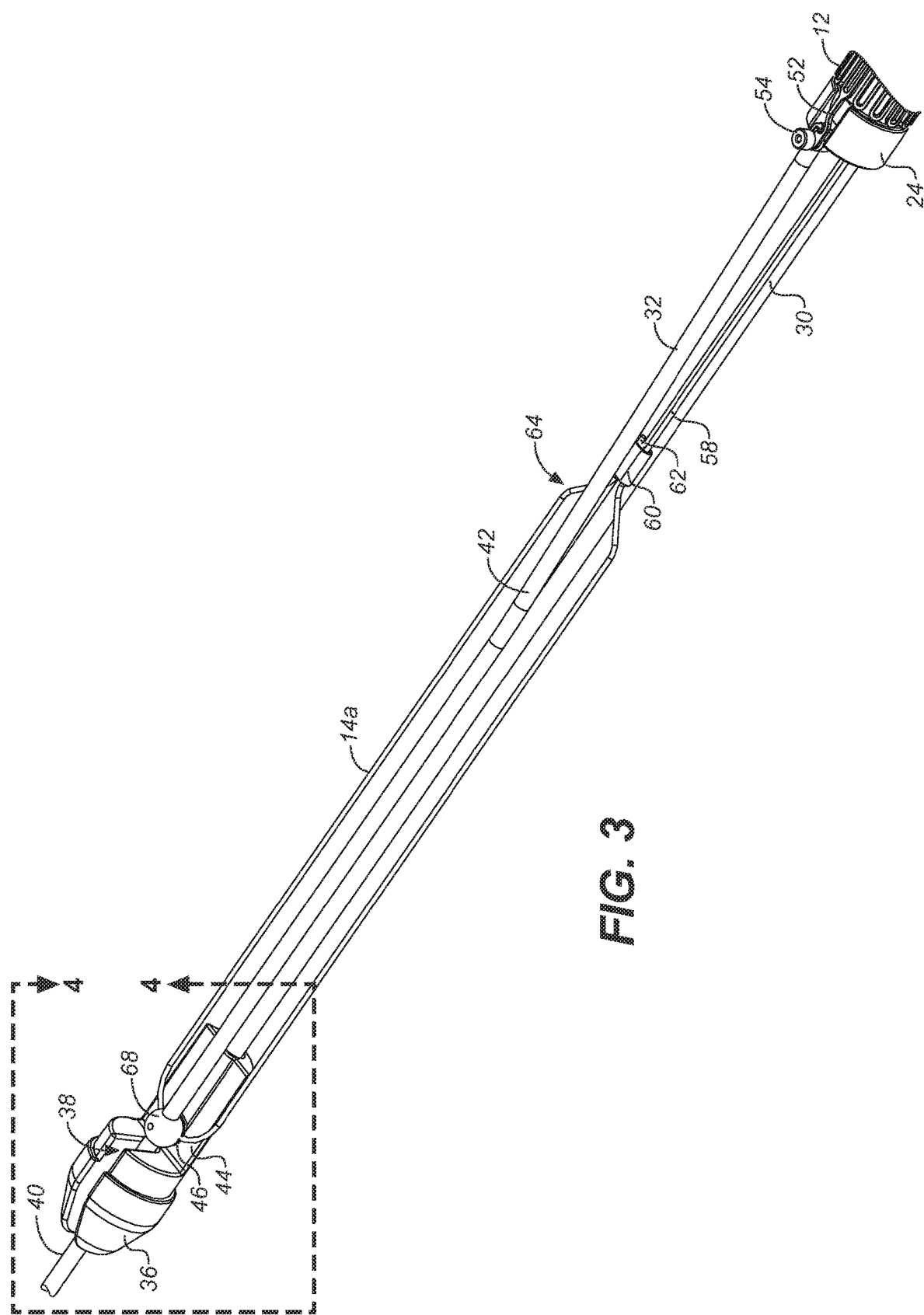
FIG. 3 is an upper perspective view showing details of the stent and the prosthesis frame mounted, respectively, on the stent carrier arrangement, the delivery system nosecone, and the guidewire insertion tool of the delivery system of FIG. 1 according to various embodiments.
Figure 4:
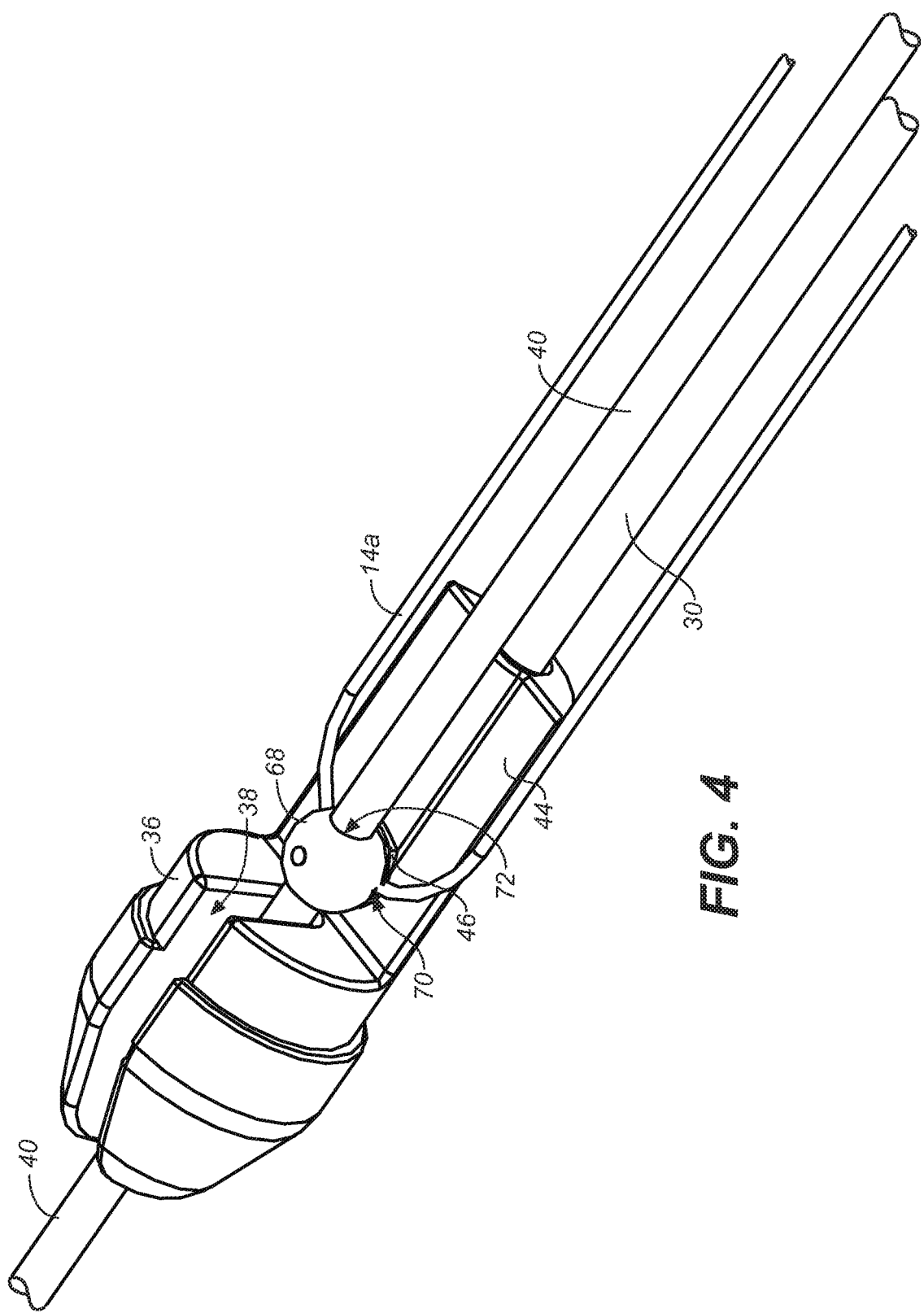
FIG. 4 is a more detailed view of the nosecone and the valve leaflet prosthesis mounting structures as taken along broken line 4-4 of FIG. 3 according to various embodiments.
Figure 14:
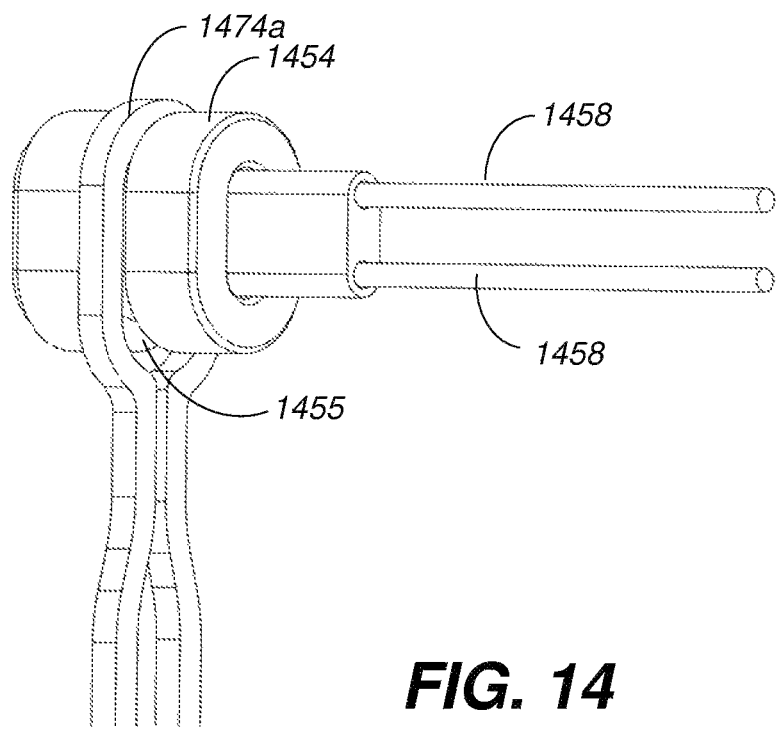
FIG. 14 is an assembly of a gimbal and a loop according to various embodiments.

According to various embodiments, the wire tether 58 (or the tether strut) as shown in FIG. 3 and FIG. 5 may be in the form of a single tether strut (as shown) in connection with the gimbal 54 or a double tether struts (as shown in FIG. 14) in connection with the gimbal 1454. According to various embodiments, one or more tether struts may connect the support frame 14a of the valve leaflet prosthesis 14 to the gimbal 54, 1454. According to various embodiments, the wire tether 58 may be connected to the gimbal 54, 1454 via connection method including, but not limited to, soldering, welding, Ultra Violet adhesive, etc. According to various embodiments, the wire tether 58 may include straight or curved struts.

FIG. 14 shows a gimbal 1454 inserted into a loop 1474a (or a connection portion of the flexible extended stent strut 50) according to various embodiments. The loop 1474a may be resilient and may define an opening into which the gimbal 1454 may be inserted. According to various embodiments, the gimbal 1454 (or the cylindrical coupling member) may be cylindrical and have an oval or elliptic cross-section. Further, the gimbal 1454 may have a continuous endless circumferential groove 1455 around an exterior cylindrical surface thereof. The loop 1474a may be engaged with the continuous endless circumferential groove 1455 of the gimbal 1454 in a manner such that the gimbal 1454 may have limited rotatability relative to the loop 1474a about the longitudinal cylinder axis of the cylindrical gimbal 1454. According to various embodiments, the loop 1474a and the continuous endless circumferential groove 1455 of the gimbal 1454 may have a loose running clearance fit such that the opening of the loop 1474a is of a larger dimension/size than a dimension/size of the continuous endless circumferential groove 1455 of the gimbal 1454. Accordingly, the gimbal 1454 may be rotatable about its longitudinal cylinder axis within a limited range of angles, and may further rock and tilt within the loop 1474a in various directions with respect the loop 1474a. According to various embodiments, the loose running clearance fit between the loop 1474a and the continuous endless circumferential groove 1455 of the gimbal 1454 may configured to allow a tilting movement of the gimbal 1454 of a range of 0° to 45°. As also shown, two tether struts 1458 may be coupled to the gimbal 1454 having the oval or elliptic cross-section.

Figure 15:
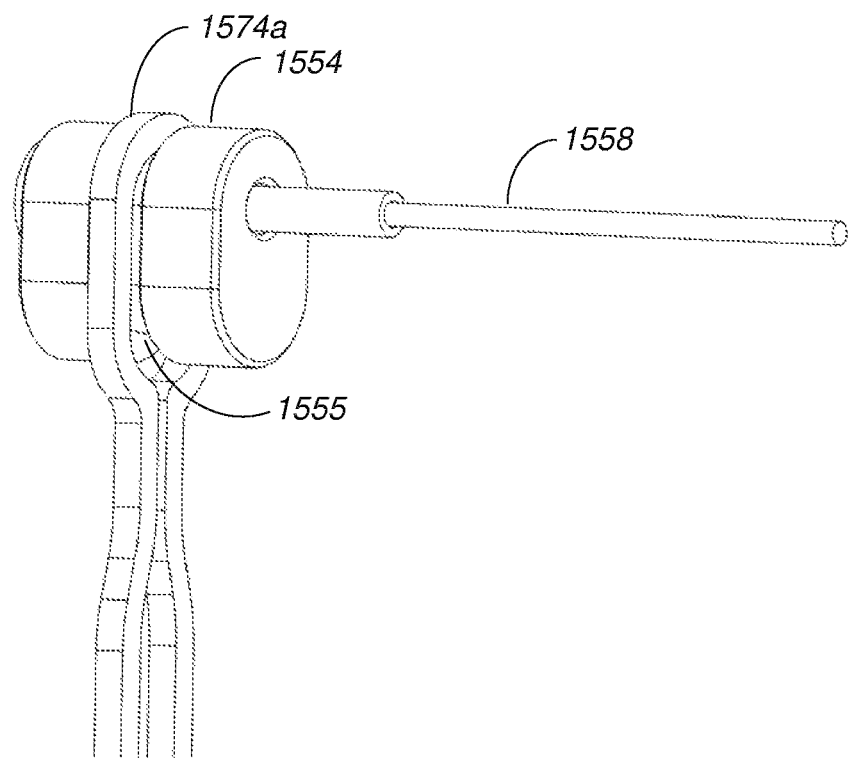
FIG. 15 is an assembly of a gimbal and a loop according to various embodiments

FIG. 15 shows a gimbal 1554 inserted into a loop 1574a (or a connection portion of the flexible extended stent strut 50) according to various embodiments. The loop 1574a is similar to the loop 1474a of FIG. 14. The gimbal 1554 is similar to the gimbal 1454 of FIG. 14 and also has a continuous endless circumferential groove 1555. The embodiment as shown in FIG. 15 differs from the embodiment as shown in FIG. 14 in that only one tether strut 1558 is coupled to the gimbal 1554 having the oval or elliptic cross-section.

Referring to FIG. 7A to 8B, according to various embodiments, the leaflet blade panel 14b of the valve leaflet prosthesis may include surgical grade fabric sutured to the respective wire frame 14a with non-absorbable braided ultra-high-molecular-weight-polyethylene (UHMWPE) or similar fiber. According to various embodiments, the respective leaflet blade panel may include guide hole arrangement, such as spherical bead 68 (or guide ball) or guide hole through the leaflet blade panel 14b. According to various embodiments, the leaflet blade panel 14b may be of various shape including, but not limited to, oval, triangular, etc. According to various embodiments, the leaflet blade panel 14b may be of single or multi-layered construct. According to various embodiments, the leaflet blade panel 14b may have a perimeter which may be straight, simple curves, scallops, etc. According to various embodiments, for multi-layered fabric configuration, the leaflet blade panel 14b may have edges that are even, offset or a mix thereof.

Referring to FIG. 1, according to various embodiments, the nosecone 36 may incorporate radiopaque markers to aid in fluoroscopic visualization for orientation and alignment. According to various embodiments the nosecone 36 may include the slot 38 for guidewire and/or guidewire insertion tool 40. According to various embodiments, the nosecone rod 30 may include braided wire with polytetrafluoroethylene (PTFE) coating. According to various embodiments, the nosecone rod 30 may include polymeric or metallic rod in a variety of shapes, hollow or solid.

According to various embodiments, the stent carrier 20 may be a single component or may be multiple subcomponents joined together to form the stent carrier 20. According to various embodiments, the stent carrier 20 may be formed by injection molding and manufacturing assembly. According to various embodiments, the stent carrier 20 may be connected to the inner catheter 16 via carrier hypo-tube or snap-fitting.

Referring to FIG. 1, according to various embodiments, the stent 12 of the valve implant may include a movement-restraining-engagement element 97 and the stent carrier 20 of the inner catheter 16 may include a corresponding movement-restraining-engagement element 99, wherein the movement-restraining-engagement element 97 of the stent 12 engages with the corresponding movement-restraining-engagement element 99 of the stent carrier 20 when the stent 12 is compressed and wrapped around the stent carrier 20 in a manner so as to restrict relative movement between the stent 12 and the stent carrier 20. According to various embodiments, the movement-restraining-engagement element 99 of the stent 12 may include hook or notch and the corresponding movement-restraining-engagement element 97 of the stent carrier 20 may include correspondingly shaped protrusions. According to various embodiments, the movement-restraining-engagement element 99 of the stent 12 may include shaped extension and the corresponding movement-restraining-engagement element 97 of the stent carrier 20 may include correspondingly shaped recesses.

Referring to FIG. 1, according to various embodiments, the outer sheath 18 may include braided sheath with liner, radiopaque band at distal end, and/or multiple braided or coiled configurations.

Various embodiments have provided a simpler and easier solution for heart valve replacement. Accordingly, the valve implant of the various embodiments may be used in heart valve replacement procedures, in particular, for tricuspid regurgitation.

The above disclosure will enable one of ordinary skill in the art to practice the invention. The disclosure provides a disclosure of embodiments of the invention. However, the embodiments do not limit the invention to the exact construction, dimensional relationships, and operation shown and described. Modifications, alternative constructions, changes and equivalents will readily occur to those skilled in the art and may be employed, as suitable, without departing from the scope of the invention Therefore, the above description and illustrations should not be construed as limiting the scope of the invention, which is defined by the appended claims

The invention claimed is:

1. A valve implant comprising:
   a valve leaflet prosthesis having a wire frame, a leaflet blade panel attached to the wire frame, and one or more tether struts extending from the wire frame;
   a stent having a first end portion and a second end portion along a longitudinal stent axis, and a flexible extended stent strut extending longitudinally from the first end portion and away from the stent; and
   a gimbal connecting the one or more tether struts of the valve leaflet prosthesis to a connection portion of the flexible extended stent strut,
   wherein the connection portion of the flexible extended stent strut comprises a loop,
   wherein the gimbal has a continuous endless circumferential groove around an exterior surface thereof,
   wherein the loop of the flexible extended stent strut is engaged with the continuous endless circumferential groove of the gimbal in a manner such that the gimbal is rotatable relative to the loop in order to
   rotatably couple the one or more tether struts of the valve leaflet prosthesis to the flexible extended stent strut in a manner such that the one or more tether struts are rotatable about a rotational axis which is parallel to the one or more tether struts and which extends transverse to the longitudinal stent axis, so as to rotate the valve leaflet prosthesis.

2. The implant as claimed in claim 1, wherein the loop is formed by a hook, the hook comprises a shank portion having a sinuous profile, followed by a bend portion, and followed by a finger portion extending alongside the shank portion in a manner so as to form a sinuous capturing slot between the shank portion and the finger portion.

3. The implant as claimed in claim 2, wherein the shank portion has at least one lobe extending towards the finger portion and the finger portion has at least one lobe extending towards the shank portion, wherein the at least one lobe of the shank portion juts over the at least one lobe of the finger portion in an overhanging manner so as to form the sinuous capturing slot meandering around the at least one lobe of the shank portion and the at least one lobe of the finger portion.

4. The implant as claimed in claim 1, wherein the gimbal is cylindrical and comprises a circular cross-section, or an oval cross-section, or an elliptic cross-section.

5. The implant as claimed in claim 1, wherein the leaflet blade panel comprises a layered arrangement of two or more layers, and wherein a first layer has a perimeter border wider than a perimeter border of a second layer.

6. The implant as claimed in claim 1, wherein the valve leaflet prosthesis comprises a guide hole arrangement at a leaflet-tip-portion of the valve leaflet prosthesis.

7. The implant as claimed in claim 6, wherein the guide hole arrangement comprises a guide hole through the leaflet blade panel of the valve leaflet prosthesis, or a bead which is coupled to the wire frame and which has a guide hole through the bead.

8. A delivery system comprising:
   a delivery device comprising
      an outer sheath,
      an inner catheter inserted into the outer sheath in a manner so as to be slidable relative to the outer sheath, wherein the inner catheter has a guidewire lumen extending throughout an entire length of the inner catheter and comprises a stent carrier arrangement at an end portion of the inner catheter,
      a nosecone assembly having a nosecone-rod extending longitudinally from an end of the inner catheter and a nosecone disposed at an end of the nosecone-rod, wherein the nosecone comprises a leaflet-prosthesis-alignment-element, and
      a guidewire insertion tool extending longitudinally and coaxially from an end of the guidewire lumen of the inner catheter so as to serve as a continuation of the guidewire lumen; and
   a valve implant comprising
      a valve leaflet prosthesis having a wire frame, a leaflet blade panel attached to the wire frame, and one or more tether struts extending from the wire frame,
      a stent having a first end portion and a second end portion along a longitudinal stent axis, and a flexible extended stent strut extending longitudinally from the first end portion and away from the stent,
      a gimbal connecting the one or more tether struts of the valve leaflet prosthesis to a connection portion of the flexible extended stent strut,
      wherein the connection portion of the flexible extended stent strut comprises a loop,
      wherein the gimbal has a continuous endless circumferential groove around an exterior surface thereof,
      wherein the loop of the flexible extended stent strut is engaged with the continuous endless circumferential groove of the gimbal in a manner such that the gimbal is rotatable relative to the loop in order to rotatably couple the one or more tether struts of the valve leaflet prosthesis to the flexible extended stent strut in a manner such that the one or more tether struts are rotatable about a rotational axis, which is parallel to the one or more tether struts and which extends transverse to the longitudinal stent axis, so as to rotate the valve leaflet prosthesis,
      wherein the stent of the valve implant is compressed to wrap around the stent carrier arrangement, the flexible extended stent strut is bent so as to align the one or more tether struts of the valve leaflet prosthesis longitudinally with respect to the stent, and the valve leaflet prosthesis of the valve implant is compressed into an elongate shape and placed in engagement with the leaflet-prosthesis-alignment-element of the nosecone.

9. The system as claimed in claim 8, wherein the stent of the valve implant comprises a movement-restraining-engagement element and the stent carrier arrangement of the inner catheter comprises a corresponding movement-restraining-engagement element, wherein the movement-restraining-engagement element of the stent engages with the corresponding movement-restraining-engagement element of the stent carrier arrangement when the stent is compressed and wrapped around the stent carrier arrangement in a manner so as to restrict relative movement between the stent and the stent carrier arrangement.

10. The system as claimed in claim 9, wherein the movement-restraining-engagement element of the stent comprises hook or notch and the corresponding movement-restraining-engagement element of the stent carrier arrangement comprises correspondingly shaped protrusions, or wherein the movement-restraining-engagement element of the stent comprises a shaped extension and the corresponding movement-restraining-engagement element of the stent carrier arrangement comprises correspondingly shaped recesses.

11. The system as claimed in claim 8, further comprising a control handle coupled to the delivery device, the control handle comprising
   a first control mechanism configured to control and actuate the inner catheter to move axially relative to the outer sheath; and
   a second control mechanism configured to control and actuate the outer sheath to move axially relative to the inner catheter.

12. The system as claimed in claim 8, wherein the valve leaflet prosthesis comprises a guide hole arrangement at a leaflet-tip-portion of the valve leaflet prosthesis, wherein the guidewire insertion tool is inserted through the guide hole arrangement of the valve leaflet prosthesis.

13. The system as claimed in claim 12, wherein the guide hole arrangement comprises a guide hole through the leaflet blade panel of the valve leaflet prosthesis, or a bead which is coupled to the wire frame and which has a guide hole through the bead.

14. A method of preparing a delivery system for delivering a valve implant, the method comprising:
   inserting a guidewire, in a front loading manner, through a guidewire insertion tool and through a guidewire lumen of an inner catheter of a delivery device of the delivery system, wherein the delivery device comprises an outer sheath,
      the inner catheter inserted into the outer sheath in a manner so as to be slidable relative to the outer sheath, wherein the inner catheter has the guidewire lumen extending throughout an entire length of the inner catheter and comprises a stent carrier arrangement at an end portion of the inner catheter,
a nosecone assembly having a nosecone-rod extending longitudinally from an end of the inner catheter and a nosecone disposed at an end of the nosecone-rod, wherein the nosecone comprises a leaflet-prosthesis-alignment-element, and
the guidewire insertion tool extending longitudinally and coaxially from an end of the guidewire lumen of the inner catheter so as to serve as a continuation of the guidewire lumen; and
removing the guidewire insertion tool from the delivery system such that the guidewire remains inserted through the guidewire lumen of the inner catheter,
wherein the valve implant comprises
a valve leaflet prosthesis having a wire frame, a leaflet blade panel attached to the wire frame, and one or more tether struts extending from the wire frame,
a stent having a first end portion and a second end portion along a longitudinal stent axis, and a flexible extended stent strut extending longitudinally from the first end portion and away from the stent, and
a gimbal connecting the one or more tether struts of the valve leaflet prosthesis to a connection portion of the flexible extended stent strut,
wherein the connection portion of the flexible extended stent strut comprises a loop,
wherein the gimbal has a continuous endless circumferential groove around an exterior surface thereof,
wherein the loop of the flexible extended stent strut is engaged with the continuous endless circumferential groove of the gimbal in a manner such that the gimbal is rotatable relative to the loop in order to rotatably couple the one or more tether struts of the valve leaflet prosthesis to the flexible extended stent strut in a manner such that the one or more tether struts are rotatable about a rotational axis, which is parallel to the one or more tether struts and which extends transverse to the longitudinal stent axis, so as to rotate the valve leaflet prosthesis,
wherein the stent of the valve implant is compressed to wrap around the stent carrier arrangement, the flexible extended stent strut is bent so as to align the one or more tether struts of the valve leaflet prosthesis longitudinally with respect to the stent, and the valve leaflet prosthesis of the valve implant is compressed into an elongate shape and placed in engagement with the leaflet-prosthesis-alignment-element of the nosecone,
wherein the valve leaflet prosthesis comprises a guide hole arrangement at a leaflet-tip-portion of the valve leaflet prosthesis,
wherein the guidewire insertion tool is inserted through the guide hole arrangement of the valve leaflet prosthesis.

15. The method as claimed in claim 14, wherein the guide hole arrangement comprises a guide hole through the leaflet blade panel of the valve leaflet prosthesis, or a bead which is coupled to the wire frame and which has a guide hole through the bead.

* * * * *